United States Patent [19]

Fukudome et al.

[11] Patent Number: 5,695,993
[45] Date of Patent: Dec. 9, 1997

[54] CLONING AND REGULATION OF AN ENDOTHELIAL CELL PROTEIN C/ ACTIVATED PROTEIN C RECEPTOR

[75] Inventors: Kenji Fukudome; Charles T. Esmon, both of Oklahoma City, Okla.

[73] Assignee: Oklahoma Medical Research Foundation, Oklahoma City, Okla.

[21] Appl. No.: 289,699

[22] Filed: Aug. 12, 1994

[51] Int. Cl.$^6$ .............................. C12N 5/16; C07H 21/04
[52] U.S. Cl. .................... 435/325; 435/69.1; 435/320.1; 536/23.5
[58] Field of Search .................... 536/23.5, 23.1, 536/24.1–24.3, 24.31; 435/69.1, 325, 320.1

[56] References Cited

U.S. PATENT DOCUMENTS

| | | |
|---|---|---|
| 3,625,214 | 12/1971 | Higuchi . |
| 4,244,946 | 1/1981 | Rivier et al. . |
| 4,305,872 | 12/1981 | Johnston et al. . |
| 4,316,891 | 2/1982 | Guillemin et al. . |
| 4,629,784 | 12/1986 | Stammer . |
| 4,789,734 | 12/1988 | Pierschbacher . |
| 4,792,525 | 12/1988 | Ruoslahti et al. . |
| 4,868,116 | 9/1989 | Morgan et al. . |
| 4,906,474 | 3/1990 | Langer et al. . |
| 4,925,673 | 5/1990 | Setiner et al. . |
| 4,980,286 | 12/1990 | Morgan et al. . |
| 5,009,889 | 4/1991 | Taylor et al. . |

OTHER PUBLICATIONS

Rothbarth et al., *J. Cell Science*, vol. 104, pp. 19–30, Jan., 1993.
Agrawal, S., et al., "Oligodeoxynucleoside Phosphoramidates and Phosphorothioates as Inhibitors of Human Immunodeficiency Virus", *Proc. Natl. Acad. Sci. USA*, 85:7079–7083 (Oct., 1988).
Askew, B., et al., "Molecular Recognition with Convergent Functional Groups. 6. Synthetic and Structural Studies with a Model Receptor for Nucleic Acid Components", *J. Am. Chem. Soc.*, 111:1082–1090 (1989).
Blume, S.W., et al., "Triple helix Formation by Purine–rich Oligonucleotides Targeted to the Human Dihydrofolate Reductase Promoter", *Nucl. Acids Res.*, 20:1777–1784 (1992).
Bock, P.E., "Active Site Selective Labeling of Serine Proteases with Spectroscopic Probes Using Thioester Peptide Chloromethyl Ketones: Demonstration of Thrombin Labeling Using N$^\alpha$–[(Acetylthio)acetyl] –D–Phe–Pro–Arg–CH$_2$Cl", *Biochemistry*, 27:6633–6639 (1988).
Clackson, T., et al., "Making Antibody Fragments Using Phage Display Libraries", *Nature*, 352:624–688 (Aug., 1991).
Conway, E.M., et al., "Tumor Necrosis Factor Suppresses Transcription of the Thrombomodulin Gone in Endothelial Cells", *Mol. Cell. Biol*, 8:5588–5592 (Dec., 1988).

Cooney, M., et al., "Site–Specific Oligonucleotide Binding Represses Transcription of the Human c–myc Gene In Vitro". *Science*, 241:458–459 (Jul., 1988).
Crooke, S.T., "Progress Toward Oligonucleotide Therapeutics: Pharmacedynamic Properties", *FASEB J.*, 7:533–539 (Apr., 1993).
Dahlbäck, B., "Protein S and C4b–Binding Protein: Components Involved in the Regulation of the Protein C Anticoagulant System", *Thromb. Haemostas.*, 66:49–61 (1991).
Dahlbäck, B., "Inhibition of Protein C$_a$ Cofactor Function of Human and Bovine Protein S by C4b–binding Protein", *J. Biol. Chem.*, 261:12022–12027 (Sep., 1986).
Dahlbäck, B., "Binding of Anticoagulant Vitamin K–Dependent Protein S to Platelet–Derived Microparticles", *Biochemistry*, 31:12769–12777 (1992).
Daugherty, B.L., et al., "Polymerase Chain Reaction Facilitates the Cloning, CDR–Grafting, and rapid Expression of a Murine Monoclonal Antibody directed Against the CD18 Component of Leukocyte Integrins", *Nucl. Acids Res.*, 19:2471–2476 (1991).
Dittman, W.A., "Thrombomodulin—Biology and Potential Cardiovascular Applications", *Trends Cardiovasc. Med.*, 1:331–336 (1991).
Dittman, W.A., et al., "Structure and Function of Thrombomodulin: A Natural Anticoagulant", *Blood*, 75:329–336 (Jan., 1990).
Dreyfus, M., et al., "Treatment of Homozygous Protein C Deficiency and Neonatal Purpura Fulminans With a Purified Protein C Concentrate", *N. Engl. J. Med.*, 325:1565–1568 (1991).
Duval–Valentin, G., et al., "Specific Inhibition of Transcription by Triple helix–forming Oligonucleotides", *Proc. Natl. Acad. Sci. USA*, 89:504–508 (Jan., 1992).
Engelman, D.M., et al., "Identifying Nonpolar Transbilayer Helices in Amino Acid Sequences of Membrane Proteins", *Annu. Rev. Biophys. Biophys. Chem.*, 15:321–53 (1986).

(List continued on next page.)

*Primary Examiner*—Paula K. Hutzell
*Assistant Examiner*—Stephen Gucker
*Attorney, Agent, or Firm*—Arnall Golden & Gregory

[57] ABSTRACT

Human protein C and activated protein C were shown to bind to endothelium specifically, selectively and saturably (Kd=30 nM, 7000 sites per cell) in a Ca$^{2+}$ dependent fashion. Expression cloning revealed a 1.3 kb cDNA that coded for a novel type I transmembrane glycoprotein capable of binding protein C. This protein appears to be a member of the CD1/MHC superfamily. Like thrombomodulin, the receptor involved in protein C activation, the endothelial cell protein C receptor (EPCR) function and message are both down regulated by exposure of endothelium to TNF. Identification of EPCR as a member of the CD1/MHC superfamily provides insights into the role of protein C in regulating the inflammatory response, and determination of methods for pharmaceutical use in manipulating the inflammatory response.

11 Claims, 10 Drawing Sheets

OTHER PUBLICATIONS

Esmon, C.T., "The Roles of Protein C and Thrombomodulin in the Regulation of Blood Coagulation", *J. Biol. Chem.*, 264:4743–4746 (Mar., 1989).

Esmon, C.T., et al., "Protein C Activation", *Meths. Enzymol.*, 222:359–385 (1993).

Esmon, C.T., "Protein S and Protein C—Biochemistry, Physiology, and Clinical Manifestation of Deficiencies", *Trends Cardiovasc. Med.*, 2:214–220 (1992).

Gerson, W.T., et al., "Severe Acquired Protein C Deficiency in Purpura Fulminans Associated With Disseminated Intravascular Coagulation: Treatment With Protein C Concentrate", *Pediatrics*, 91:418–422 (Feb., 1993).

Graham, F.L., et al., "A New Technique for the Assay of Infectivity of Human Adenovirus 5 DNA", *Virology*, 52:456–467 (1973).

Gregoriadis, G., "Liposomes", *Drug Carriers in Biology and Medicine*, 287–341 (Academic Press, 1979).

Grey, S., et al., "Selective Effects of Protein C on Activation of Human Monocytes by Lipopolysaccharide, Interferon–Y, or PMA: Modulation of Effects on CD11b and CD14 but not CD25 or CD54 Induction", *Transplant. Proc.*, 25:2913–2914 (Oct., 1993).

Grigoriev, M., et al., "A Triple Helix–forming Oligonucleotide–Intercalator Conjugate Acts as a Transcriptional Repressor via Inhibition of NF κB Binding to Interleukin–2 Receptor α–Regulatory Sequence", *J. Biol. Chem.*, 267:3389–3395 (Feb., 1992).

Grinnell, B.W., et al., "Human Protein C Inhibits Selectin––mediated Cell Adhesion: Role of Unique Fucosylated Oligosaccharide", *Glycobiology*, 4:221–226 (1994).

Hogg, P.J., et al., "Identification of Structural Domains in Protein C Involved in its Interaction with Thrombin–Thrombomodulin on the Surface of Endothelial Cells", *J. Biol. Chem.*, 267:703–706 (Jan., 1992).

Holt, J.T., et al., "An Oligomer Complementary to c–myc mRNA Inhibits Proliferation of HL–60 Promyelocytic Cells and Induces Differentiation", *Mol. Cell Biol.*, 8:963–973 (Feb., 1988).

Ikuta, K., et al., "Synthesis and Use of Synthetic Oligonucleotides", *Ann. Rev. Biochem.*, 53:323–356 (1984).

Kaisho, T., et al., "BST–1, A Surface Molecule of Bone Marrow Stromal Cell Lines That Facilitates Pre–B–Cell Growth", *Proc. Natl. Acad. Sci. (USA)*, 91:5325 (Jun., 1994).

Kapiotis, S., et al., "Interleukin–4 Counteracts Pyrogen–Induced Downrequlation of Thrombomodulin in Cultured Human Vascular Endothelial Cells", *Blood*, 78:410–415 (Jul., 1991).

Kozak, M., "Point Mutations Define a Sequence Flanking the AUG Initiator Codon That Modulates Translation by Eukaryotic Ribosomes", *Cell*, 44:283–292 (Jan., 1986).

Kyte, J., et al., "A Simple Method for Displaying the Hydropathic Character of a Protein", *J. Mol. Biol.*, 157:105–132 (1982).

Le Bonniec, B.F., et al., "The Role of Calcium Ions in Factor X Activation by Thrombin E192Q", *J. Biol. Chem.*, 267:6970–6976 (Apr., 1992).

Ledbetter, J.A., et al., "Covalent Association Between Human Thymus Leukemia–like Antigens and CDB(Tp32) Molecules", *J. Immunol.*, 134:4250–4254 (Jun., 1985).

Lentz, S.R., et al., "Regulation of Thrombomodulin by Tumor Necrosis Factor–α: Comparison of Transcriptional and Posttranscriptional Mechanisms", *Blood*, 77:543–550 (Feb., 1991).

Lewis, R.A., et el., "Automated Site–directed Drug Design: The Concept of Spacer Skeletons for Primary Structure Generation", *Proc. R. Soc. Lond.*, 236:125–140 and 141–182 (1989).

Maciag, T., et al., "An Endothelial Cell Growth Factor From Bovine Hypothalamus: Identification and Partial Characterization", *Proc. Natl. Acad. Sci. (USA)*, 76:5674–5678 (Nov., 1979).

Maher, L.J., et al., "Inhibition of DNA Binding Proteins by Oligonucleotide–Directed Triple Helix Formation", *Science*, 245:725–730 (Aug., 1989).

Maruyama, I., et al., "Increased Expression of Thrombomodulin on the Cultured Human Umbilical Vein Endothelial Cells and Mouse Hemangioma Cells by Cyclic AMP", *Thrombosis Research*, 61:301–310 (1991).

McKinaly, J.A., et al., "Rational Design of Antiviral Agents", *Annu. Rev. Pharmacol. Toxicol.*, 29:111–122 (1989).

Merrifield, R.B., "Solid Phase Peptide Synthesis. I. The Synthesis of a Tetrapeptide", *J. Am. Chem. Soc.*, 85:2149 (1964).

Mizushima, S., et al., "EF–BOS, A Powerful Mammalian Expression Vector", *Nucleic Acids Res.*, 18:5322 (1990).

Moore, K.L., et al., "Tumor Necrosis Factor Leads to the Internalization and Degradation of Thrombomodulin From the Surface of Bovine Aortic Endothelial Cells in Culture", *Blood*, 73:159–165) (Jan., 1989).

Mulligan, R.C., "The Basic Science of Gene Therapy", *Science*, 260:926–932 (May, 1993).

Nerang, S.A., et al., "Chemical of Deoxyoligonucleotides by the Modified Triester–Method", *Methods Enzymol.*, 65:610–620 (1980).

Nawroth, P.P., "Modulation of Endothelial Cell Hemostatic Properties by Tumor Necrosis Factor", *J. Exp. Med.* 163:740–745 (Mar., 1986).

Offensperger, W–B, et. al., "In Vivo Inhibition of Duck Hepatitis B Virus Replication and Gene Expression by Phosphorothioate Modified Antisense Oligodeoxynucleotides", *EMBO J.*, 12:1257–1262 (1993).

Olsen, P.H., et al., "$Ca^{2+}$ Dependence of the Interactions Between Protein C, Thrombin, and the Elastase Fragment of Thrombomodulin. Analysis by Ultracentrifugation", *Biochemistry*, 31:746–754 (1992).

Orson, F.M., et al., "Oligonucleotide Inhibition of IL2Rα mRNA Transcription by Promoter Region Collinear Triplex Formation in Lymphocytes", *Nucl. Acids Res.*, 19:3435–3441 (1991).

Panja, A., et al., "CD1d Is Involved in T Cell–Intestinal Epithelial Cell Interactions", *J. Exp. Med.* 178, 1115–1119 (Sep., 1993).

Perry, et al., *QSAR: Quantitative Structure–Activity Relationships in Drug Design*, 189–193 (Alan R. Liss, Inc., 1989).

Porcelli, S., et al., "CD1b Restricts the Response of Human CD48T Lymphocytes to a Microbial Antigen", *Nature*, 360:593–597 (Dec., 1992).

Postel, E.H., et al., "Evidence That a Triplex–forming Oligodeoxyribonucleotide Binds to the c–myc Promoter in HeLa Cells, Thereby Reducing c–myc mRNA Levels", *Proc. Natl. Acad. Sci. USA*, 88:8227–8231 (Sep., 1991).

Proudfoot, N.J., "3' Non–coding Region Sequences in Eukaryotic Messenger RNA", *Nature*, 263:211–214 (Sep., 1976).

Rezaie, A.R., et al., "The High Affinity Calcium–binding Site Involved in Protein C Activation is Outside the First Epidermal Growth Factor Homology Domain", *J. Biol. Chem.*, 267:11701–11704 (Jun. 15, 1992).

Ripka, W., "Computers Picture the Perfect Drug", *New Scientist*, 54–57 (Jun. 16, 1988).

Rothbarth, K., et al., "cDNA–derived Molecular Characteristics and Antibodies to a New Centrosome–associated and $G_2$/M Phase–prevalent Protein", *J. Cell Sci.*, 104:19–30 (1993).

Rotivinen, et al., *Acta Pharmaceutica Fennica*, 97:159–166 (1988).

Sarin, P.S., et al., "Inhibition of Acquired Immunodeficiency Syndrome Virus by Oligodeoxynucleoside Methylphosphonates", *Proc. Natl. Acad. Sci. USA*, 85:7448–7794 (1989).

Seligsohn, U., et al., "Homozygous Protein C Deficiency Manifested by Massive Venous Thrombosis in the Newborn", *N. Engl. J. Med.*, 310:559–562 (Mar., 1984).

Shaw, J–P, et al., "Modified Deoxyoligonucleotides Stable to Exonuclease Degradation in Serum", *Nucleic Acids Res.* 19:747–750 (1991).

Stern, D.M., et al., "Cultured Bovine Aortic Endothelial Cells Promote Activated Protein C–Protein S–Mediated Inactivation of Factor V", *J. Biol. Chem.*, 261:713–718 (Jan., 1986).

Szostak, J.W., "In Vitro Genetics", *TIBS*, 19:89 (1992).

Taylor, F.B., et al., "Protein C Prevents the Coagulopathic and Lethal Effects of *Escherichia coli* Infusion in the Baboon", *J. Clin. Invest.*, 79:918–925 (Mar., 1987).

Taylor, F., et al., "C4b–Binding Protein Exacerbates the Host Response to *Escherichia coli*", *Blood*, 78:357–363 (Jul., 1991).

von Heijne, G., "A New Method for Predicting Signal Sequence Cleavage Sites", *Nucleic Acids Res.*, 14:4683–4690 (1986).

Wickstrom, E.L., "Human Promyelocytic Leukemia HL–60 Cell Proliferation and c–myc Protein Expression are Inhibited by an Antisense Pentadecadeoxynucleotide Targeted Against c–myc mRNA", *Proc. Natl. Acad. Sci. USA*, 85:1028–1032 (Feb., 1988).

Williams, A.F., "The Immunoglobulin Superfamily—Domains for Cell Surface Recognition", *Ann. Rev. Immunol.*, 6:381–405 (1988).

Young, S.L., et al., "Triple Helix Formation Inhibits Transcription Elongation In Vitro", *Proc. Natl. Acad. Sci. USA*, 88:10023–10026 (Nov., 1991).

Zamecnik, P.C., et al., "Inhibition of Rous Sarcoma Virus Replication and Cell Transformation by a Specific Oligodeoxynucleotide", *Proc. Natl. Acad. Sci. USA*, 75:280–284 (Jan., 1978).

Zamecnik, P.C., et al., "Inhibition of Replication and Expression of Human T–cell Lymphotropic Virus Type III in Cultured Cells by Exogenous Synthetic Oligonucleotides Complementary to Viral RNA", *Proc. Natl. Acad. Sci.*, 83:4143–4146 (Jun., 1986).

Zhu, N., et al., "Systemic Gene Expression After Intravenous DNA Delivery Into Adult Mice", *Science*, 261:209–211 (Jul., 1993).

Bangalore, N. et al., "High Affinity Binding Sites for Activated Protein C and Protein C on Cultured Human Umbilical Vein Endothelial Cells", *Thrombosis and Haemostasis*, vol. 72, no. 3, pp. 465–474 (1994).

Fukudome, K. et al., "Molecular Cloning and Expression of Murine and Bovine Endothelial Cell Protein C/activated Protein C Receptor (EPCR)", *J. Biological Chemistry*, vol. 270, no. 10, pp. 5571–5577 (1995).

Fukudome, K. et al., "Identification, Cloning, and Regulation of Novel Endothelial Cell Protein C/activated Protein C Receptor", *Circulation*, vol. 90, no. 4, pt. 2, pp. I–N, I133 (1994).

Fukudome, K. et al., "Identification, Cloning, and Regulation of Novel Endothelial Cell Protein C/activated Protein C Receptor", *J. Biological Chemistry*, vol. 269, No. 42, pp. 26486–26491 (1994).

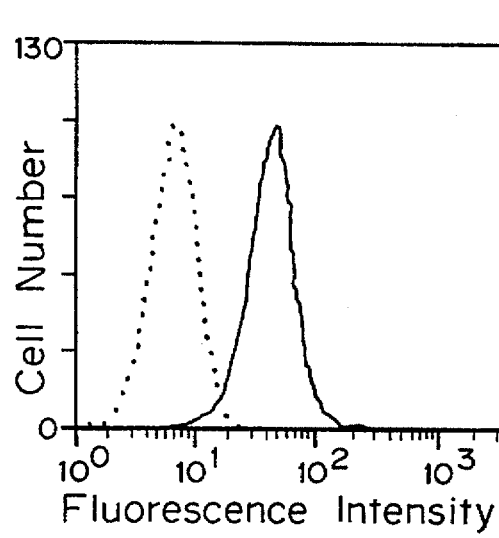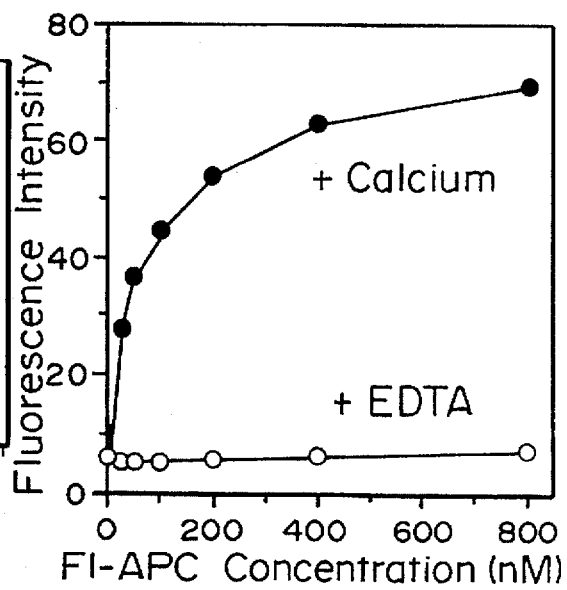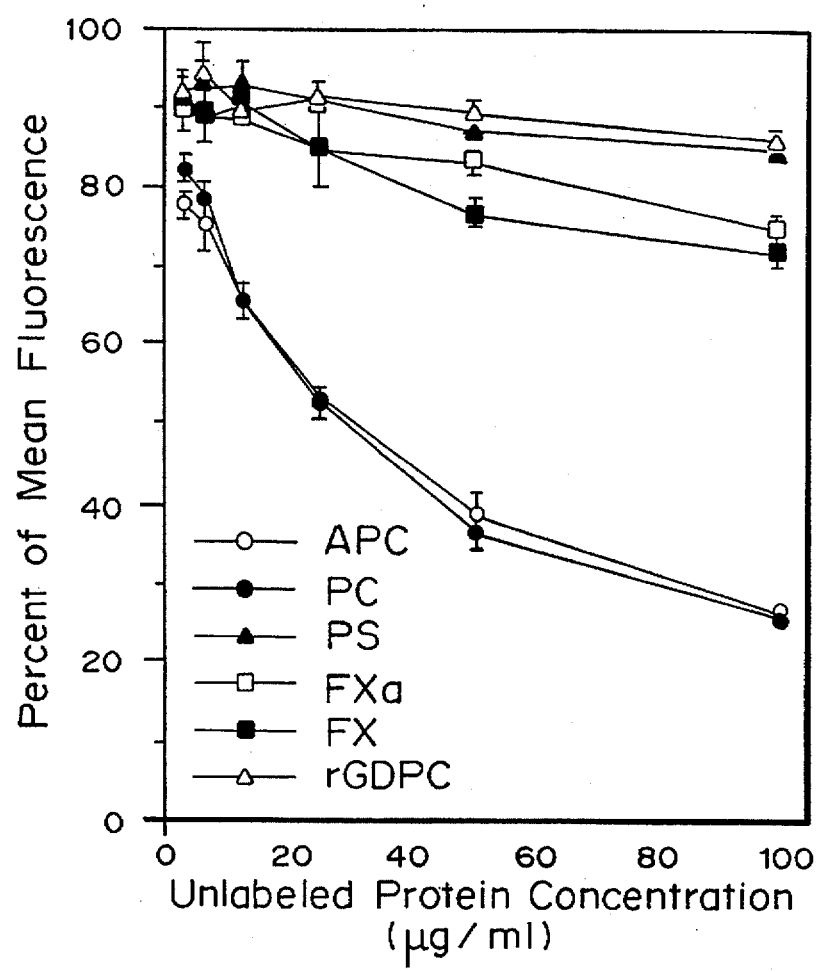

FIG. 4a

```
CAGGTCCGGAGCCTCAACTTCAGGATGTTGACAACATTGCTGCCGATACTGCTGCTGTCT    60
                       M  L  T  T  L  L  P  I  L  L  L  S       12

GGCTGGGCCTTTTGTAGCCAAGACGCCTCAGATGGCCTCCAAAGACTTCATATGCTCCAG   120
 G  W  A  F  C  S  Q  D  A  S  D  G  L  Q  R  L  H  M  L  Q     32

ATCTCCTACTTCCGGGACCCTATCACGTGTGGTACCAGGGCAACGCGTCGCTGGGGGGA   180
 I  S  Y  F  R  D  P  Y  H  V  W  Y  Q  G  N  A  S  L  G  G     52

CACCTAACGGCACGGTGCTGGAAGGCCCAGACACCAACACCAGAGATCATTCAGCTGCAGCCC   240
 H  L  T  H  V  L  E  G  P  D  T  N  T  T  I  I  Q  L  Q  P     72

TTGCAGGAGCCCGAGAGCTGGGCCCGCACGCAGAGTGGCCTGCAGTCCTACCTGCTCCAG   300
 L  Q  E  P  E  S  W  A  R  T  Q  S  G  L  Q  S  Y  L  L  Q     92

TTCCACGGCCTCGTGCGCCTGGTGCACCAGGAGCGGACCTTGGCCTTTCCTCTGACCATC   360
 F  H  G  L  V  R  L  V  H  Q  E  R  T  L  A  F  P  L  T  I    112

CGCTGCTTCCTGGGCTGTGAGCTGCCTCCCGAGGGCTCTAGAGCCCATGTCTTCTTCGAA   420
 R  C  F  L  G  C  E  L  P  P  E  G  S  R  A  H  V  F  F  E    132
```

FIG. 4b

```
GTGGCTGTGAATGGGAGCTCCTTTGTGAGTTTCCGGCCGGAGAGAGCCTTGTGGCAGGCA  480
 V  A  V  N  G  S  S  F  V  S  F  R  P  E  R  A  L  W  Q  A    152

GACACCCAGGTCACCTCCGGAGTGGTCACCTTCACCCTGCAGCAGCTCAATGCCTACAAC  540
 D  T  Q  V  T  S  G  V  V  T  F  T  L  Q  Q  L  N  A  Y  N    172

CGCACTCGGTATGAACTGCGGGAATTCCTGGAGGACACCTGTGTGCAGTATGTGCAGAAA  600
 R  T  R  Y  E  L  R  E  F  L  E  D  T  C  V  Q  Y  V  Q  K    192

CATATTTCCGCCGAAAACACGAAAAGGGAGCCAAACAAGCCGTCCTACACTTCGCTGGTC  660
 H  I  S  A  E  N  T  K  G  S  Q  T  S  R  S  Y  T  S  L  V    212

CTGGGCGTCCTGGTGGGCGGGTTTCATCATTGCTGGTGTGGCTGTAGGCATCTTCCTGTGC  720
 L  G  V  L  V  G  G  F  I  I  A  G  V  A  V  G  I  F  L  C    232

ACAGGTGGACGGCGGATGTTAATTACTCTCCAGCCCCGTCAGAAGGGGCTGGATTGATGGA  780
 T  G  G  R  R  C  *                                            238
```

FIG. 4C

```
GGCTGGGCAAGGGAAAAGTTTCAGCTCACTGTGAAGCCAGACTCCCAACTGAAAACACCAGA   840
AGGTTTGGAGTGACAGCTCCTTCTCTCCCACATCTGCCCACTGAAGATTTGAGGGAGG        900
GGAGATGGAGAGGAGAGGTGGACAAAGTACTTGGTTTGCTAAGAACCTAAGAACGTGTAT     960
GCTTTGCTGAATTAGTCTGATAAGTGAATGTTATCTATCTTTGTGGAAAACAGATAATG     1020
GAGTTGGGCAGGAAGCCTATGCGCCATCCTCCAAAGACACAGAATCACCTGAGGCGT        1080
TCAAAAGATATAACCAAATAAACAAGTCATCCACAATCAAAATACAACATTCAATACTTC    1140
CAGGTGTGTCAGACTTGGGATGGGACGCTGATATAATAGGGTAGAAAGAAGTAACACGAA    1200
GAAGTGGTGGAAATGTAAAATCCAAGTCATATGGCAGTGATCAATTAATCAATTAAT        1260
AATATTAATAAATTTCTTATATTTAAAAAAAAAAAAAAAAAA  1302
```

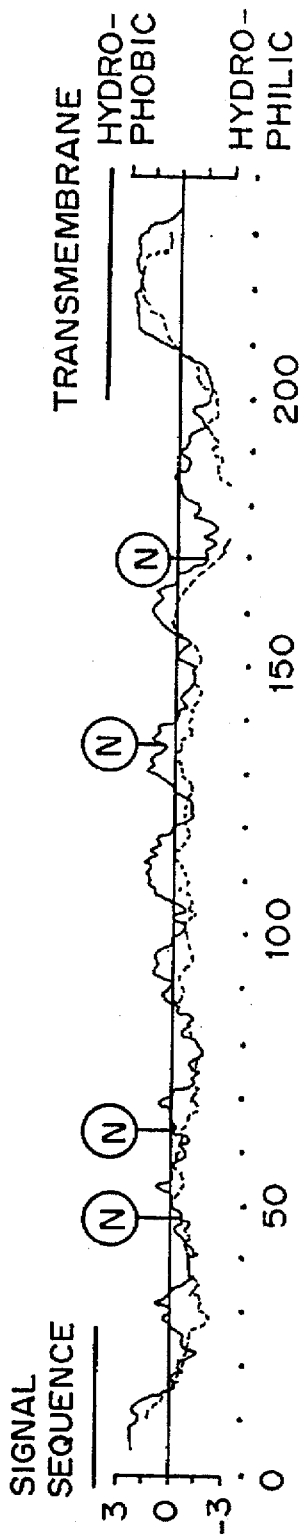

FIG. 5a

```
EPCR    MLTT..LLPILLLSGWAFCSQDASDGLQRLHMLQISYFRDPYHVWYQGNASLGGHLTHVL
CCD41   MLTKFLLLLLLLLPGCAFVTPMAPKAAYAPDLL....FPRPPSCEASGQRSLGKLLTHTL
CD1d    MGC...LLFLLLWALLQAWGSAEVPQRLFPLRCLQISSFANSSWTRTDGLAWGELQTHSW
MCD1.2  MRY...LPCLLLWAFLQVWGQSEVQQKNYTFRCLQTSSFANISWSRTDSLILLGDLQTHRW

EPCR    EGPDTNTTIIQLQPLQEPESWARTQSGLQSYLLQFHGLVRLVHQER......TLAFPLTI
CCD41   EGPSQNVTILQLQPWQDPESWERTESGLQIYLTQFESLVKLVYRER....KENVFFPLTV
CD1d    SN...DSDTVRSLRPWSQGTFSDQQWETLQHIFRVYRSSFTRDVKEFAKML...RLSYPLEL
MCD1.2  SN...DSATISFTKPWSQGKLSNQQWEKLQHMFQVYRVSFTRDIQELVKMMSPKEDYPIEI

EPCR    RCFLGCEL.P...PEGSRAHVFFEVAVNGSSFVSFRPERALWQADTQVTSGVTFTLQQL
CCD41   SCSLGCEL.PEEEEGSEPHVFFDVAVNGSAFVSFRPKTAVWSGSQEPSKAANFTLKQL
CD1d    QVSAGCEVHP......GNASNNFFHVAFQGKDILSFQGTS..WEP.TQEAPLWNLAIQVL
MCD1.2  QLSTGCEMYP......GNASESFFHVAFQGKYAVRFRGTS..WQR.VLGAPSWLDLPIKVL
```

FIG. 5b

```
         *  *   **         * ***                **
EPCR     ................NAYNRTRYELREFLEDTCVQYV.............
CCD41    ................NAYNRTRYELQEFLQDTCVEFL.............
CD1d     NQDKWTRETVQWLLNGTCPQFVSGLLESGKSELKKQVKPKAWLSRGPSPGRLLLVCHVSG
MCD1.2   NADQGTSATVQTLLNDTWPQFARGLLEAGKSDLEKQEKPVAWLSSVPSSAHGHLQLVCHVSG

**         * *
EPCR     ...........................................
CCD41    ...........................................
CD1d     FYPKPVWKWMRGEQEQQGTQPGDILPNADETWYLRATLDVVAGEAAGLSCRVKHSSLEG
MCD1.2   FYPKPVWMWMRGDQEQQGTHRGDFLPNADETWYLQATLDVEAGEEAGLACRVKHSSLGG

****  * ***                    *                **
EPCR     .........RSYTSLVLGVLVGGFIIAGVAVGIFLCTGGRRC........
CCD41    .........RSYTSLVLGILMGCFIIAGVAVGIFMCTSGRGLLII.....
CD1d     QDIVLYWGGSYTSMGLIALAVLACLLFLLIVGFTS.RFKRQTSYQGVL
MCD1.2   QDIILYWDARQAPVGLIVFIVLIMLVVVGAVVYYI.WRRRSAYQDIR
```

EPCR  
CCD41  
CD1d  
MCD1.2

```
1 MLTTLLP..ILLLSGWAFCSQDASDGLQRLHMLQISYFRDPYHVWYQGNA 48
  |||-||  :|||-||:|-  |||-|| ||||||-|..||:.||||
1 MLTKFLPLLLLLLPGCALCN...SDGSQSLHMLQISYFQDHHHVRHQGNA 47

49 SLGGHLTHVLEGPDTNTTIIQLQPLQEPESWARTQSGLQSYLLQFHGLVR 98
   |||  |||-||||-|-|:||||:|:|||.||-:|||||| ||.:||:
48 SLGKLLTHTLEGPSQNVTILQLQPWQDPESWERTESGLQIYLTQFESLVK 97

99 LVHQER..TLAFPLTIRCFLGCELP...PEGSRAHVFFEVAVNGSSFVSF 143
   ||-||  ..:||||--| ||||||    -|||:||||:||||||-||||
98 LVYRERKENVFFPLTVSCSLGCELPEEEEEGSEPHVFFDVAVNGSAFVSF 147

144 RPERALWQADTQVTSGVVTFTLQQLNAYNRTRYELREFLEDTCVQYVQKH 193
    ||.|:|..|.|...|||.||||||||||.|||:||||:....|
148 RPKTAVWVSGSQEPSKAANFTLKQLNAYNRTRYELQEFLQDTCVEFLENH 197

194 ISAENTKGSQTSRSYTSLVLGVLVGGFIIAGVAVGIFLCTGGRRC 238
    |..:|||||:|||||||:|-| ||||||||||-||-||||
198 ITTQNMKGSQTGRSYTSLVLGILMGCFIIAGVAVGIFMCTSGRRC 242
```

FIG. 6

CLONING AND REGULATION OF AN ENDOTHELIAL CELL PROTEIN C/ACTIVATED PROTEIN C RECEPTOR

BACKGROUND OF THE INVENTION

The present invention is generally in the area of cloning, expression, and regulation of an endothelial cell protein C/activated protein C receptor.

Protein C plays a major role in the regulation of blood coagulation. Patients deficient in protein C usually exhibit life threatening thrombotic-complications in infancy (Seligsohn et al., (1984) *N. Engl. J. Med.* 310, 559–562; Esmon, (1992) *Trends Cardiovasc. Med.* 2, 214–220) that are corrected by protein C administration (Dreyfus et al., (1991) *N. Engl. J. Med.* 325, 1565–1568). In addition, activated protein C (APC) can prevent the lethal effects of *E. coli* in baboon models of gram negative sepsis (Taylor et al., (1987) *J. Clin. Invest.* 79; U.S. Pat. No. 5,009,889 to Taylor and Esmon) and preliminary clinical results suggest that protein C is effective in treating certain forms of human septic shock (Gerson et al., (1993) *Pediatrics* 91, 418–422). These results suggest that protein C may both control coagulation and influence inflammation. Indeed, inhibition of protein S, an important component of the protein C pathway, exacerbates the response of primates to sublethal levels of *E. coli* and augments the appearance of TNF in the circulation (Taylor et al., (1991) *Blood* 78, 357–363). The mechanisms involved in controlling the inflammatory response remain unknown.

Protein C is activated when thrombin, the terminal enzyme of the coagulation system, binds to an endothelial cell surface protein, thrombomodulin (Esmon, (1989) *J. Biol. Chem.* 264, 4743–4746; Dittman and Majerus, (1990) *Blood* 75, 329–336; Dittman, (1991) *Trends Cardiovasc. Med.* 1, 331–336). In cell culture, thrombomodulin transcription is blocked by exposure of endothelial cells to tumor necrosis factor (TNF) (Conway and Rosenberg, (1988) *Mol. Cell. Biol.* 8, 5588–5592) and thrombomodulin activity and antigen are subsequently internalized and degraded (Lentz et al., (1991) *Blood* 77, 543–550, Moore, K. L., et al., (1989) *Blood* 73, 159–165). In addition, C4bBP, a regulatory protein of the complement system, binds protein S to form a complex that is functionally inactive in supporting APC anticoagulant activity in vitro (Dahlbäck, (1986) *J. Biol. Chem.* 261, 12022–12027) and in vivo (Taylor, et al., 1991). Furthermore, C4bBP behaves as an acute phase reactant (Dahlbäck, (1991) *Thromb. Haemostas.* 66, 49–61). Thus, proteins of this pathway not only appear to regulate inflammation, but they also interact with components that regulate inflammation, and they themselves are subject to down regulation by inflammatory mediators.

Given the central role of the protein C pathway in regulating the host response to inflammation and the critical role of the pathway in controlling blood coagulation, it is important to identify and characterize all of the components that interact with the system. This is especially true since the molecular basis of the anti-inflammatory effects of the protein C pathway components have yet to be elucidated at the molecular level.

It is therefore an object of the present invention to provide a cellular receptor for protein C and activated protein C.

It is a further object of the present invention to provide nucleotide sequences encoding the cellular receptor and amino acid characterization of the receptor which allows expression of recombinant native and modified forms of the receptor.

It is another object of the present invention to provide methods of modulating the inflammatory response involving protein C and activated protein C.

SUMMARY OF THE INVENTION

An endothelial cell protein C binding protein (referred to herein as "EPCR") has been cloned and characterized. The protein is predicted to consist of 238 amino acids, which includes a 15 amino acid signal sequence at the N-terminus, and a 23 amino acid transmembrane region which characterizes the receptor as a type 1 transmembrane protein. The protein binds with high affinity to both protein C and activated protein C (Kd=30 nM) and is calcium dependent. The message and binding function of the receptor are both down regulated by cytokines such as TNF.

These results identify a new member of a complex pathway that, like other members of the pathway, is subject to regulation by inflammatory cytokines, and can therefore be used to modulate inflammatory reactions in which protein C or activated protein C is involved. Inhibition of the inflammatory response can be obtained by infusing soluble EPCR. Alternatively, localizing EPCR to surfaces in contact with blood will render the surfaces anticoagulant by virtue of the ability of EPCR to bind and concentrate the anticoagulant activated protein C at the surface. Alternatively, the function of EPCR can be enhanced by overexpressing the EPCR in endothelium that could be used to coat vascular grafts in patients with vascular disease or on stents in cardiac patients.

BRIEF DESCRIPTION OF THE DRAWINGS

FIGS. 1A, 1B and 1C are flow cytometric analyses of F1-APC (fluorescent labelled activated protein C) binding to HUVEC (human umbilical vein endothelial cells). FIG. 1A is a graph of cell number versus log of fluorescence intensity, demonstrating F1-APC binding to HUVEC. HUVEC ($1 \times 10^5$) were incubated at room temperature without (dotted line) or with 160 nM of F1-APC (solid line) in the presence of 1.3 mM $CaCl_2$. After washing, bound APC was analyzed by flow cytometry. FIG. 1B is a graph of fluorescence intensity versus F1-APC concentration (nM) demonstrating the concentration dependence of F1-APC binding to HUVEC. HUVEC were incubated with F1-APC in the absence (open circles) or presence of 1.3 mM $CaCl_2$ (closed circles) and binding was measured as in A. Mean channel fluorescence intensity is plotted for each F1-APC concentration (between 0 and 800 nM). FIG. 1C is a graph of the percent of mean fluorescence versus unlabeled protein concentration (µg/ml), demonstrating the effects of unlabeled proteins on F1-APC binding to HUVEC. F1-APC binding to HUVEC was carried out in the presence of the indicated concentrations (between 0 and 100 µg/ml) of unlabeled APC, protein C, protein S, factor X and Xa or recombinant Gla-domainless protein C (rGDPC).

FIG. 2A is a graph of the bound APC ($cpm \times 10^{-3}$) versus time (min), showing the time course of $^{125}$I-APC binding to HUVEC. HUVEC monolayers ($1.2 \times 10^5$ cells) were incubated at 4° C. with 32 nM (filled squares) or 8 nM (open squares) $^{125}$I-APC. At the indicated times, cells were washed and bound radioactivity was measured. FIG. 2B is a graph of bound APC ($cpm \times 10^{-3}$) versus unlabeled protein (nM) demonstrating the effects of unlabeled APC and rGDPC on $^{125}$I-APC binding to HUVEC. HUVEC were incubated at 4° C. for one hour with $^{125}$I-labeled APC in the presence of the indicated concentrations (between 01 and approximately 1000 nM) of unlabeled APC (open circles) or rGDPC (closed circles). After washing, bound radioactivity was measured. FIG. 2C is a graph of bound APC (fmol/well) versus free APC (nM) demonstrating the concentration dependence of $^{125}$I-APC binding to HUVEC. Monolayers of HUVEC were incubated with the concentrations of $^{125}$I-APC indicated as described above. Specific binding was determined as described below. FIG. 2D is a Scatchard analysis of $^{125}$I-APC binding to HUVEC. Each value was calculated from the data shown in FIG. 2C.

FIG. 4 is the predicted protein structure of EPCR based on nucleotide sequence Sequence ID No. 1, predicted amino acid sequence, Sequence ID No. 2, and a hydropathy plot of EPCR. The signal sequence and transmembrane region are indicated with the solid bars.

FIG. 5 is a comparison of the amino acid sequence of EPCR to the amino acid sequences of other members of the CD1 family and CCD41. The EPCR sequence, Sequence ID No. 2, is shown in the first line and compared to murine CCD41, Sequence ID No. 3, (second line), human CD1d, Sequence ID No. 4, (third line) and murine CD1.2, Sequence ID No. 5, (fourth line). Identities with EPCR are indicated by open boxes. Residues that are conserved between EPCR and all of the human CD1 family members are indicated by a double asterisk. Residues shared with one or more members of the CD1 family are indicated by a single asterisk.

FIG. 6 is a comparison of the amino acid sequence of human EPCR, Sequence ID No. 2, (first line) to the amino acid sequence of murine EPCR, Sequence ID No. 6, (second line). Identities are indicated by boxes. Similarities are indicated with an asterisk.

DETAILED DESCRIPTION OF THE INVENTION

I. Cloning and Characterization of EPCR

Figure 2A:
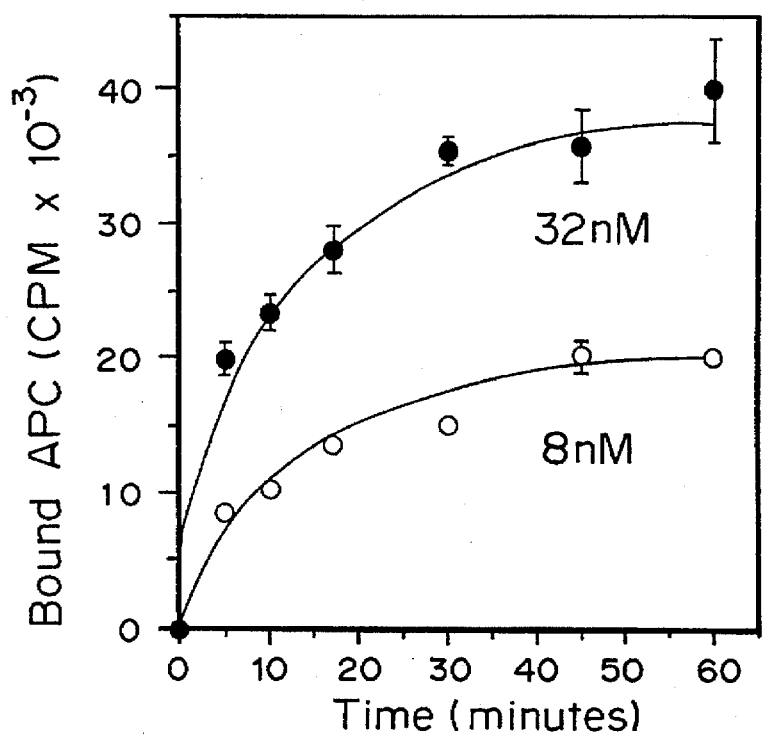
FIGS. 2A, 2B, 2C and 2D are graphs of $^{125}$I-APC Binding to HUVEC Monolayers.

Human protein C and activated protein C are shown to bind to endothelium specifically, selectively and saturably (Kd=30 nM, 7000 sites per cell) in a $Ca^{2+}$ dependent fashion. FL-APC binding to various human cell lines were examined, and found that the binding was HUVEC specific. A human kidney cell line transformed with SV40 large T antigen, 293T cells, expressed very few of these binding sites. A HUVEC cDNA library was constructed using the powerful mammalian expression vector, pEF-BOS (Mizushima and Nagata, (1990) *Nucleic Acids Res.* 18, 5322). Plasmid DNA was prepared from subpools of independent colonies (2,500 colonies per pool), and transfected into 293T cells, using the method of Kaisho et al., (1994) *Proc. Natl. Acad. Sci. (USA)* 91, 5325. FL-APC binding was analyzed on a flow cytometer. One of eight subpools gave a positive signal. This subpool was divided into 20 subpools and rescreened. After three rounds of enrichment, one positive clone, EPCR-1, was isolated. EPCR-1 carries a 1.3 kb insert. When transfected into 293T cells, this clone was capable of expressing the calcium-dependent binding site for FL-APC on the 293T cell surface.

Expression cloning revealed a 1.3 kb cDNA that coded for a type I transmembrane glycoprotein capable of binding protein C. This protein appears to be a member of the CD1/MHC superfamily. Like thrombomodulin, the receptor involved in protein C activation, the endothelial cell protein C receptor (EPCR) function and message are both down regulated by exposure of endothelium to TNF. Identification of EPCR as a member of the CD1/MHC superfamily provides insights into the role of this receptor for protein C in regulating the inflammatory response.

Materials and Methods

Protein Preparation

Human protein C (Esmon et al., (1993) *Meths. Enzymol.* 222, 359–385), APC (Esmon et al., 1993), recombinant gla domainless protein C (rGDPC) (Rezaie et al., (1992) *J. Biol. Chem.* 267, 11701–11704), protein S (Taylor et al., 1991), factor X and factor Xa (Le Bonniec et al., (1992) *J. Biol. Chem.* 267, 6970–6976) were prepared as described in the cited publications.

Selective labeling of the active site of APC with fluorescein was performed by the method of Bock (Bock, P. E. (1988) *Biochemistry* 27, 6633–6639). In brief, N$^{60}$[(acetylthio)acetyl]-D-Phe-Pro-Arg-CH$_2$Cl (200 µM) was reacted with 40 µM APC for 1 hour at room temperature. After dialysis, the covalently modified APC was incubated at room temperature for one hour with 200 µM 5-(iodoacetamido)fluorescein (Molecular Probes). Free fluorescein was removed by gel filtration on a PD-10 column (Pharmacia). With this method, each molecule of fluoresceinated APC (FI-APC) contains a single dye at the active site and hence all of the fluorescent molecules behave identically.

Iodogen (Pierce) was used to radiolabel APC with Na[$^{125}$I] (Amersham) according to the manufacture's protocol in the presence of 5 mM CaCl$_2$. Free $^{125}$I was removed by gel filtration on a PD-10 column. The specific activity of the $^{125}$I-APC was 1×10$^4$ cpm/ng protein.

Cell Culture

Human umbilical vein endothelial cells (HUVEC) were isolated from fresh umbilical-cords by collagenase treatment and cultured in medium 199 containing 15% fetal bovine serum, 10 µg/ml heparin, and 0.5% endothelial cell growth supplement prepared from bovine brain extract (Maciag at al., (1979) *Proc. Natl. Acad. Sci. (USA)* 76, 5674–5678). HOS (ATCC CRL 1543), HEp-2 (ATCC CCL 23) and 293 cells (ATCC CRL 1573) transformed with SV40 large T antigen (293T, a gift from Dr. Kenji Oritani) were maintained in Earl's MEM supplemented with 10% fetal bovine serum. The human lymphocyte cell lines, Jurkat, MOLT3 (ATCC CRL 1552), Jijoye (ATCC CCL 87), Raji (ATCC CCL 86), U-937 (ATCC CRL 1593), HL-60 (ATCC CCL 240), and HEL (ATCC TIB 180), were maintained in RPMI-1640 medium supplemented with 10% fetal bovine serum.

Flow Cytometric Analysis of F1-APC Binding to Cells

Adherent cells were harvested by incubation at 37° C. for 5 min in phosphate buffered saline (PBS) containing 0.02% EDTA. Cells were washed twice with EDTA/PBS and then once with Hank's balanced salt solution (HBSS). They were resuspended in HBSS containing 1% bovine serum albumin (BSA) and 0.02% sodium azide (binding buffer). Cells (1×10$^5$) were incubated at room temperature for 45 min with F1-APC in the dark. After washing, they were resuspended in the binding buffer containing 0.5 µg/ml of propidium iodide. Bound F1-APC was analyzed on a flow cytometer, FACScan (Becton Dickinson). Living cells were gated on a dot plot display of forward-scatter (FSC) versus fluorescence-2 (FL2), and F1-APC binding was detected on the fluorescence-1 (FL-1) channel. All experiments were performed in duplicate.

$^{125}$I-APC binding to HUVEC

Monolayers of HUVEC in 24-well microplates (Costar) (1×10$^5$ cells per well) were washed twice with EDTA/PBS and once with ice-cold HBSS. Cells were then incubated at 4° C. for one hour in the binding buffer with $^{125}$I-APC. After washing three times with ice-cold HBSS, cells were released with the EDTA buffer, and the bound radioactivity was measured in a gamma counter (Isodata 500). To determine non-specific, calcium-independent adsorption of radioactivity, the cells were washed with EDTA/PBS and residual radioactivity in the cell pellet was measured. Non-specific binding of radioactivity was consistently less than 5% of the specific binding. The data was analyzed using the Enzfitter program (Elsevier Biosoft, Cambridge, U.K.).

Construction of HUVEC CDNA Library

Poly-A RNA was isolated from HUVEC (1×10$^8$ cells) using the FastTrack™ mRNA isolation kit (Invitrogen). cDNA was synthesized from 3 µg of poly-A RNA using a Librarian™ I kit (Invitrogen). A BstX I adaptor was ligated, double stranded cDNA was fractionated by agarose gel electrophoresis, and cDNA longer than 700 bp was ligated into a mammalian expression vector, pEF-BOS (Mizushima and Nagata, 1990; this vector was a kind gift from Dr. S. Nagata). The construct was transfected into *E. coli* DH10B by electropotation (Bio-Rad Gene Pulser™). The library-consisted of 8×10$^6$ independent colonies with an average size of 2.0 kb.

Expression Cloning and Sequence Analysis

Approximately 2×10$^4$ independent colonies were divided into eight subpools (each containing 2,500 independent colonies) and plasmid DNA was prepared from each subpool. Sub-confluent 293T cells in 24-well microplates were transfected with 1 µg of the DNA by the calcium/phosphate method (Graham and Van Der Eb, (1973) *Virology* 52, 456–467). After 20 hours, the medium was changed, and culture was continued for another 24 hours. The subpools were screened for F1-APC binding by FACS analysis as described above. The positive library pool was then divided into 20 new pools and rescreened. After three rounds of screening, 96 individual clones were tested and one positive clone was identified.

The insert (1.3 kb) was subcloned into pBluescript™ (Stratagene), and the nucleotide sequence was determined using a Sequenase™ version 2.0 DNA Sequencing kit (USB). Nucleotide and protein database search employed the BLAST™ (NCBI) and FASTA™ programs (GCG) with GenBank, EMBL, and SwissProt databases.

Northern Blot Analysis

Total RNAs (15 µg) from various cells were isolated, electrophoresed through formaldehyde agarose gels and transferred to a nylon membrane (Hybond-N™, Amersham). The 483 bp Xba I fragment from the 5' end of the EPCR cDNA was labeled by random priming according to the manufacturer's instructions (Multiprime™ DNA labeling system, Amersham) and used for hybridization.

Protein C and APC Binding to HUVEC

Endothelial cells in suspension bound FL-APC, as monitored by flow cytometry, and demonstrated in FIG. 1A. Binding was saturable and Ca$^{2+}$ dependent, as shown by FIG. 1B. Optimal binding required at least 1 mM Ca$^{2+}$. FL-APC was displaced from the cell surface by APC and protein C equivalently, as shown by FIG. 1C. The homologous Gla-domain containing proteins, protein S, factor X, and its active form, factor Xa, failed to displace bound F1-APC, suggesting that there is a specific binding site for APC on the endothelial cell surface. Protein C binding was dependent on the Gla domain, since recombinant gla-domainless protein C (rGDPC) failed to displace F1-APC.

Figure 2B:
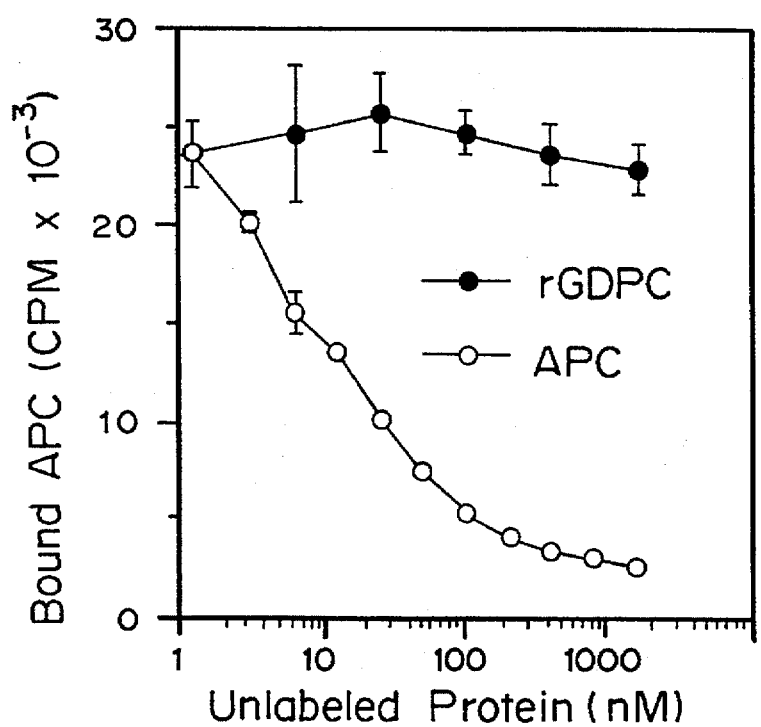
Figure 2C:
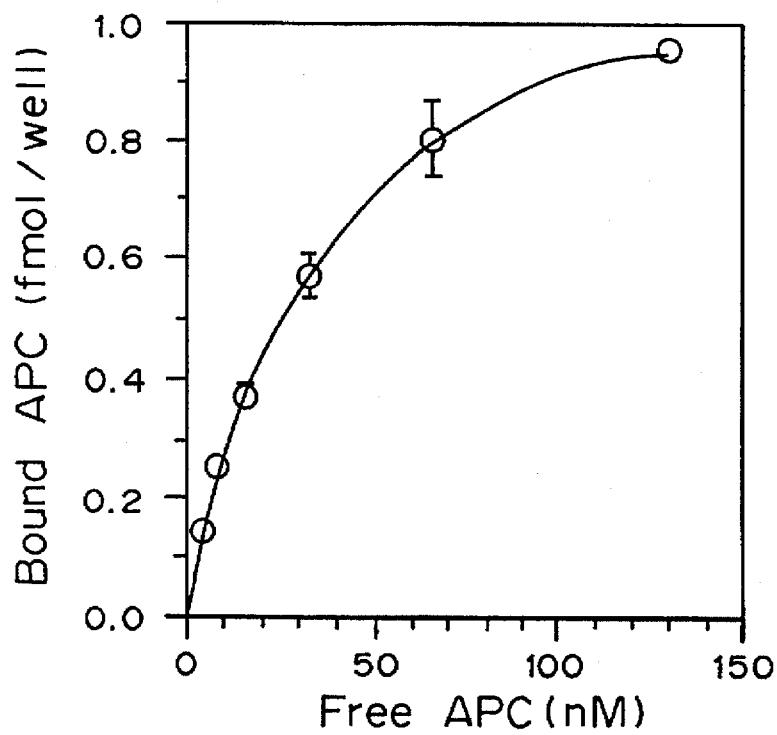
Figure 2D:
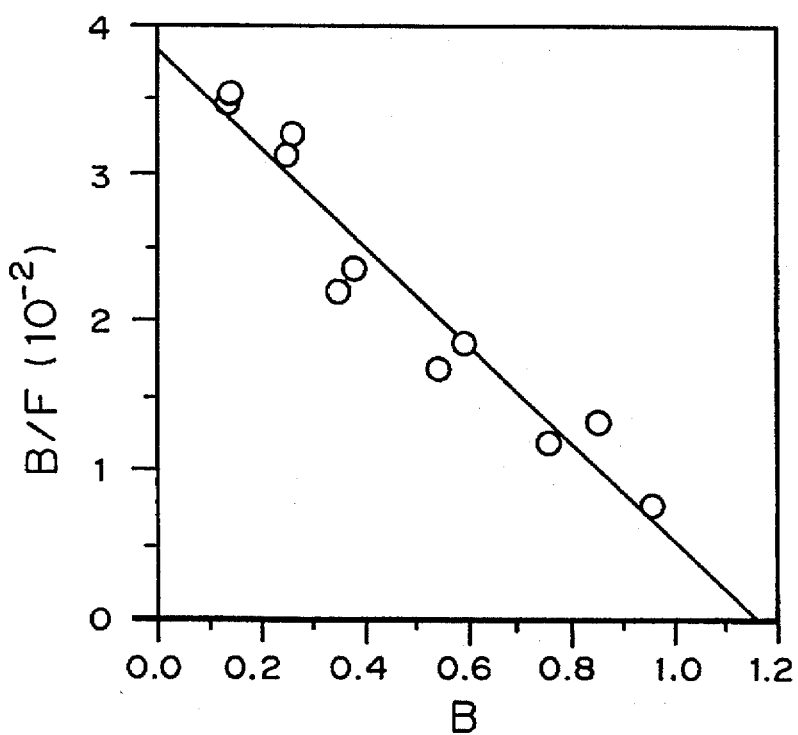
Figure 3A:
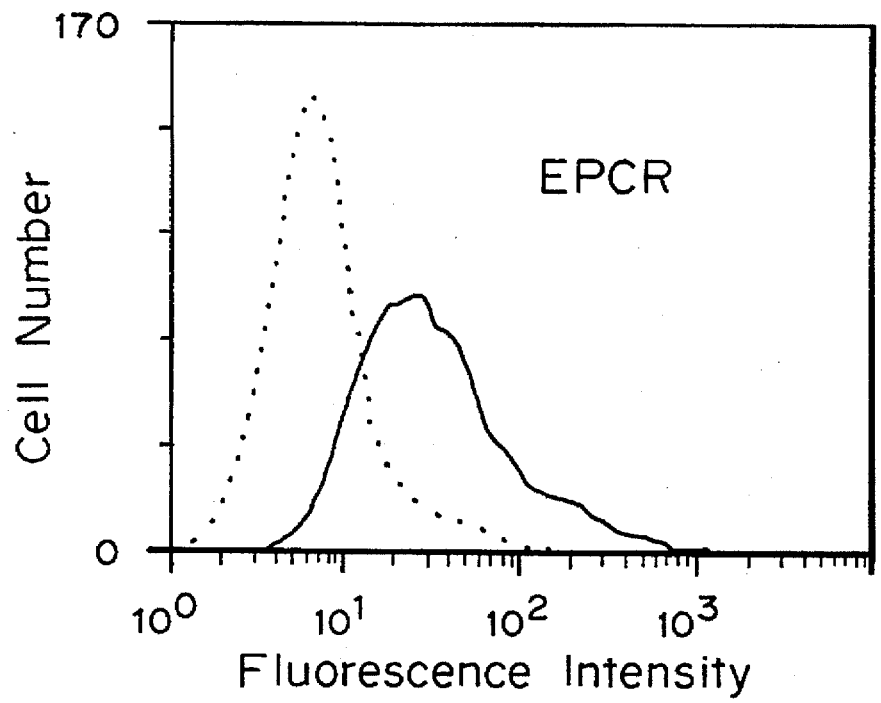
FIGS. 3A and 3B are flow cytometric analyses of F1-APC binding to 293T cells transfected with a cDNA clone of EPCR. Cells were transfected with a clone EPCR/pEF-BOS or pEF-BOS (negative control) by the calcium/phosphate method. After 24 h, cells were harvested and F1-APC binding was performed in the absence (dotted lines) or presence of 1.3 mM CaCl2 (solid lines).
Figure 3B:
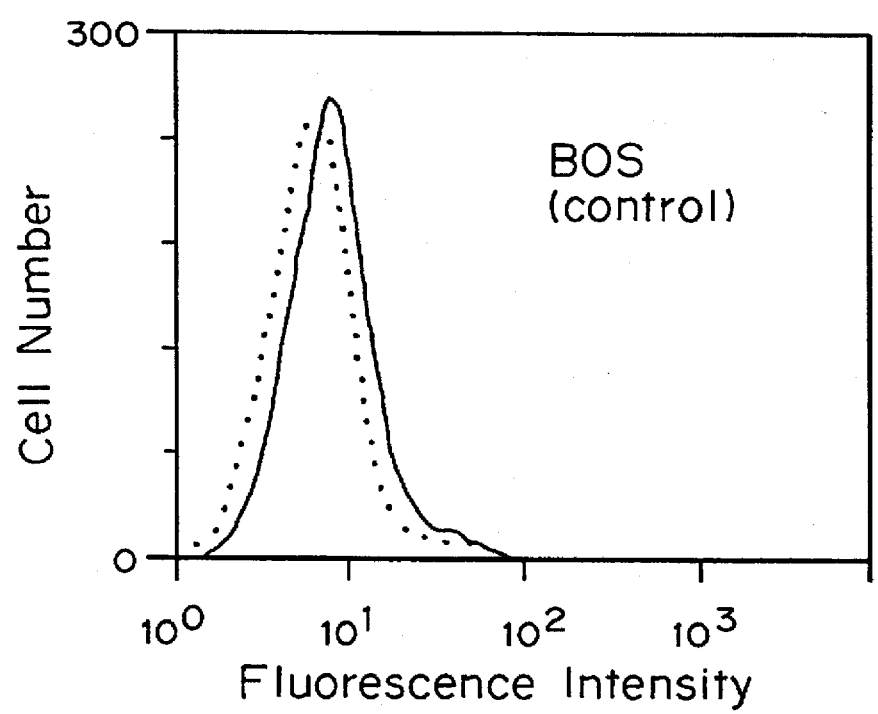

Detailed binding studies were also performed with $^{125}$I-labeled APC and monolayers of HUVEC, as shown by FIGS. 2A, 2B, 2C and 2D. The binding analysis indicated 7,000 sites per cell and a Kd=30 nM. This affinity is similar to that estimated from FIG. 1.

Endothelial cell surface thrombomodulin can interact with protein C and APC. The Kd (greater than 1 µM) (Hogg et al., (1992) *J. Biol. Chem.* 267, 703–706; Olsen et al., (1992) *Biochemistry* 31, 746–754), however, is much higher than that of the binding site described above with respect to the new receptor. Furthermore, polyclonal and monoclonal antibodies against thrombomodulin that inhibit protein C activation did not inhibit the binding. Protein S also can interact with protein C and APC (Dahlbäck et al., (1992) *Biochemistry* 31, 12769–12777), but F1-APC binding to HUVEC was not influenced by protein S addition. Furthermore, polyclonal and monoclonal antibodies to protein S did not inhibit the binding. These results indicate the binding site for protein C and APC on endothelium is distinct from these known molecules.

Nucleotide and Predicted Protein Structure Analysis of EPCR

The insert was subcloned into pBluescript, and the nucleotide sequence was determined, as shown in Sequence ID No. 1. The cDNA shown in Sequence ID No. 1 consists of 1302 bp, including a translation initiation ATG codon (AGGATGT, (Kozak, (1986) *Cell* 44, 283–292) at the 5'-end at nucleotides 25–27 of Sequence ID No. 1. A potential polyadenylation signal sequence, AATAAA, (Proudfoot and Brownlee, (1976) *Nature* 263,211–214) begins at nucleotide 1267 of Sequence ID No. 1, just 18 bp upstream of the poly(A) sequence.

The cDNA is predicted to code for a protein of 238 amino acids (Sequence ID No. 2), which includes a 15 amino acid signal sequence (von Heijne, (1986) *Nucleic Acids Res.* 14, 4683–4690) at the N-terminal. Therefore, the mature protein is predicted to contain 223 amino acids. Sequence ID No. 2 is the predicted amino acid sequence of EPCR. Amino acids 1–15 of Sequence ID No. 2 (MLTTLLPILLLSGWA) are the putative signal sequence determined by the method of von Heijne (von Heijne, 1986). Amino acids 211–236 of Sequence ID No. 2 (LVLGVLVGGFIIAGVAVGIFLCTGGR) are the putative transmembrane domain. Potential N-glycosylation sites are present at amino acids 47–49, 64–66, 136–138, and 172–174 of Sequence ID No. 2. Extracellular cysteine residues are present at amino acids 17, 114, 118, and 186 of Sequence ID No. 2. A potential transmembrane region (Engelman et al., (1986) *Annu. Rev. Biophys. Biophys. Chem.* 15, 321–53) consisting of 23 amino acids was identified at the C-terminal end (beginning at amino acid 216 of Sequence ID No. 2).

The protein is predicted to be a type 1 transmembrane protein. The extracellular domain contains four potential N-glycosylation sites and four Cys residues. The cytoplasmic region contains only three amino acids and terminates with a Cys, which could be acylated to something or involved in heterodimer formation with another peptide.

Although described with reference to cloning and expression of the protein encoding sequence, larger amounts of protein can be obtained by expression in suitable recombinant host systems, such as mammalian, yeast, bacteria, or insect cells. Isolation can be facilitated by making antibodies to the recombinant protein which are then immobilized on substrates for use in purification of additional receptors, as described below.

As used herein, the nucleotide sequences encoding the receptor include the sequence shown in Sequence ID No. 1, and sequences having conservative substitutions, additions or deletions thereof which hybridize to Sequence ID No. 1 under stringent conditions. As used herein, the amino acids sequences constituting the receptor include the sequence shown in Sequence ID No. 2, and sequences having conservative substitutions, additions or deletions thereof which form a receptor having functionally equivalent biological activity. It is well known to those skilled in the art what constitutes conservative substitutions, additions or deletions, and which could be readily ascertained as encoding, or forming, a functionally equivalent receptor molecule using the functional assays described herein.

The hydropathic plot shown in FIG. 4 was performed according to the method of Goldman et al (Engelman et al., 1994) (solid line) and that of Kyte and Doolittle (1982) *J. Mol. Biol.* 157, 105–132 (dotted line).

DNA and protein database searches revealed that the sequence is related to the centrosome-associated, cell cycle dependent murine protein, CCD41, also referred as centrocyclin (Rothbarth et al., (1993) *J. Cell Sci.* 104, 19–30), as shown by FIG. 5. The similarity in the published sequence of murine CCD41 with human EPCR led to the cloning and sequencing of the murine EPCR. The sequence of murine EPCR is shown in FIG. 6. It is distinct from the published sequence of CCD41.

The EPCR amino acid sequence was also related to, but quite distinct from, the CD1/MHC superfamily and the murine CD1.2, as also shown by FIG. 5. Based on the homology to CD1/MHC, it is likely that EPCR contains two domains consisting of residues 17–114 and 118–188. Of the CD1 family members, CD1d is the most similar to EPCR. In the mouse, CCD41 is associated exclusively with the centrosome during $G_1$ but becomes detectable elsewhere during the cell cycle, reaching a maximum during $G_2$, except during the $G_2$/M phase (Rothbarth et al., 1993). EPCR expression appears restricted to endothelium, which would not be expected for a cell cycle associated protein.

The identification of the protein C receptor on endothelium suggests that the endothelial cell binds protein C/APC through three distinct mechanisms. In addition to EPCR, protein S can bind APC/protein C on negatively charged membrane surfaces that include the endothelium (Stern et al., (1986) *J. Biol. Chem.* 261, 713–718), but this is not cell type specific (Dahlbäck et al., 1992). Thrombomodulin in complex with thrombin can bind protein C and APC (Hogg et al., 1992). On endothelium, the protein S binding sites (Nawroth and Stern, (1986) *J. Exp. Med.* 163, 740–745), thrombomodulin (Esmon, 1989) and EPCR are all down regulated by cytokines, indicating that inflammation can impair protein C pathway function at multiple levels.

The homology to the CD1/MHC family of proteins is especially interesting since it provides indications as to the function of EPCR. The CD1/MHC family has three extracellular domains termed α1,2 and 3. The extracellular domain of EPCR contains four Cys residues that appear to correspond to two distinct domains. EPCR lacks the third domain of the CD1/MHC family, but the two domains have significant homology to the α1 and α2 domains of the CD1 protein family and the α2 domain of the MHC class 1 protein, suggesting that these proteins evolved from a common ancestor. The first domain of EPCR, residues 17–114, contains two potential N glycosylation sites and is rich in β strand structure, suggesting that it may form a β sheet. Despite the β strand structure, consensus sequences (Williams and Barclay, (1988) *Ann. Rev. Immunol.* 6, 381–405) for the immunoglobulin superfamily of receptors are absent. The second domain of EPCR, residues 118–188, contains two additional N glycosylation sites and, like the CD1/MHC family, this domain is predicted to have limited β structure.

II. Modulation of Inflammation using EPCR.

In vitro studies have suggested anti-inflammatory activities for APC. For instance, an unusual carbohydrate sequence on protein C can inhibit inflammatory cell adhesion to selectins (Grinnell at al., (1994) *Glycobiology*, 4, 221–226) Modest inhibitory effects of APC have been reported on TNF production (Grey et al., (1993) *Transplant. Proc.* 25, 2913–2914). EPCR could contribute to these anti-inflammatory mechanisms. Since the homologous protein family, CD1, can be linked to CD8 (Ledbetter et al., (1985) *J. Immunol.* 134, 4250–4254), it is also possible that the proteins C receptor is linked to another protein and signal through this second protein. One of the CD1 family members, CD1d, has been reported to promote T cell responses, possibly involving binding to CD8 (Panja et al., (1993) *J. Exp. Med.* 178, 1115–1119). CD1b has recently been reported to serve as an antigen presenting molecule (Porcelli et al., (1992) *Nature* 360, 593–597). The ability to bind protein C/APC could then be linked either directly or indirectly to signalling via direct interaction with cells of the immune system. Since the MHC class of proteins is involved in presentation of proteins to cell receptors, the concept of presentation of protein C/APC to inflammatory cells as a means of elaborating anti-inflammatory activity may also be involved. This includes modulation of enzyme specificity such as occurs with thrombin-thrombomodulin interaction (Esmon, 1989). In this case, the EPCR-APC complex might cleave biologically active peptides from unknown substrates.

EPCR mRNA Levels and APC Binding

To determine the cellular specificity of EPCR expression, the intensity of FL-APC binding to HUVEC was compared to several human cell lines. F1-APC bound strongly only to HUVEC, and not to any of the T, B, or monocytic cell lines tested. Cells were incubated at room temperature without or with 160 nM F1-APC in the presence of 1.3 mM $CaCl_2$. Binding was analyzed by flow cytometry. Slight binding was demonstrated with the osteosarcoma line, HOS and the epidermoid carcinoma cell line, HEp-2.

Total RNA was extracted from these cells and hybridized with the EPCR cDNA probe for Northern Blot Analysis. EPCR mRNA was detected by Northern blot analysis for HUVEC, Jurkat, HEp-2, Raji, HOS, and U937. Among the cells lines tested, EPCR mRNA was detected at high levels only in HUVEC. The calculated mRNA size of 1.3 kb was identical to the size of the isolated cDNA. After prolonged exposure, a weak signal was also detected with the osteosarcoma cell line HOS and monocyte cell line U937. Thus, both APC binding and EPCR mRNA expression are very specific for endothelium.

Effects of TNF on APC Binding and EPCR MRNA Levels

Several other members of the protein C anticoagulant pathway are subject to regulation by inflammatory cytokines (Esmon, 1989). For instance, endothelial cell surface thrombomodulin expression and message are known to be reduced by exposure of the cells to TNF (Conway and Rosenberg, 1988; Lentz et al., 1991). To determine if a similar process occurs with EPCR, HUVEC were treated with TNF and APC binding and expression of EPCR mRNA were examined. APC binding to HUVEC decreased in a time dependent fashion. EPCR activity decreased more rapidly than thrombomodulin antigen. HUVEC were cultured for 0, 6, 24 and 48 hr, in the presence of TNF-α (10 ng/ml). Cells were harvested and residual F1-APC binding or thrombomodulin (TM) expression was analyzed by flow cytometry. Cell surface TM was stained with an anti-TM murine monoclonal antibody and FITC-conjugated anti-mouse IgG. The negative control is without added fluorescent ligand.

HUVEC were treated with 10 ng/ml of TNF-α for 0, 0.5, 1, 2, 3, 6, 10 and 24 hr, and message was extracted and detected as described above. The results demonstrated that the concentration of EPCR mRNA was also reduced by TNF treatment. Message levels and APC binding activity decreased in parallel. Therefore, the TNF mediated down-regulation of APC binding to endothelium probably occurs at the level of mRNA expression.

Enhancement of inflammatory responses by blocking binding of endogenous molecules to ECPCR can be achieved by administration of compounds binding to the receptor to a subject in need of inhibition. The degree of binding is routinely determined using assays such as those described above. Compounds which are effective include antibodies to the protein, fragments of antibodies retaining the binding regions, and peptide fragments of APC which include the Gla region. Inhibition of the inflammatory response could be obtained by infusing soluble EPCR. Alternatively, localizing EPCR to surfaces in contact with blood would render the surfaces anticoagulant by virtue of the ability of EPCR to bind and concentrate the anticoagulant APC at the surface. Alternatively, the function of EPCR could be enhanced by overexpressing the EPCR in endothelium used to coat vascular grafts in patients with vascular disease or on stents in cardiac patients.

The DNA sequence can also be used for screening for other homologous or structurally similar receptor proteins using hybridization probes.

These methods and reagents and pharmaceuticals are more readily understood by reference to the following.

Screening of patient samples for expression of receptor proteins.

Patients with thrombosis or hyperinflammatory conditions could be screened for defects in the EPCR gene. Sequence ID No. 1, and consecutive portions thereof of at least about seven nucleotides, more preferably fourteen to seventeen nucleotides, most preferably about twenty nucleotides, are useful in this screening using hybridization assays of patient samples, including blood and tissues. Screening can also be accomplished using antibodies, typically labelled with a fluorescent, radiolabelled, or enzymatic label, or by isolation of target cells and screening for binding activity, as described in the examples above. Typically, one would screen for expression on either a qualitative or quantitative basis, and for expression of functional receptor. Labelling can be with $^{32}P$, $^{35}S$, fluorescein, biotin, or other labels routinely used with methods known to those skilled in the art for labelling of proteins and/or nucleic acid sequences.

Hybridization Probes

Reaction conditions for hybridization of an oligonucleotide probe or primer to a nucleic acid sequence vary from oligonucleotide to oligonucleotide, depending on factors such as oligonucleotide length, the number of G and C nucleotides, and the composition of the buffer utilized in the hybridization reaction. Moderately stringent hybridization conditions are generally understood by those skilled in the art as conditions approximately 25° C. below the melting temperature of a perfectly base-paired double-stranded DNA. Higher specificity is generally achieved by employing incubation conditions having higher temperatures, in other words, more stringent conditions. In general, the longer the sequence or higher the G and C content, the higher the temperature and/or salt concentration required. Chapter 11 of the well-known laboratory manual of Sambrook et al., MOLECULAR CLONING: A LABORATORY MANUAL, second edition, Cold Spring Harbor Laboratory Press, New York (1990) describes hybridization conditions for oligonucleotide probes and primers in great detail, including a description of the factors involved and the level of stringency necessary to guarantee hybridization with specificity.

The preferred size of a hybridization probe is from 10 nucleotides to 100,000 nucleotides in length. Below 10 nucleotides, hybridized systems are not stable and will begin to denature above 20° C. Above 100,000 nucleotides, one finds that hybridization (renaturation) becomes a much slower and incomplete process, as described in greater detail in the text MOLECULAR GENETICS, Stent, G. S. and R. Calender, pp. 213–219 (1971). Ideally, the probe should be from 20 to 10,000 nucleotides. Smaller nucleotide sequences (20–100) lend themselves to production by automated organic synthetic techniques. Sequences from 100–10,000 nucleotides can be obtained from appropriate restriction endonuclease treatments. The labeling of the smaller probes with the relatively bulky chemiluminescent moieties may in some cases interfere with the hybridization process.

Generation of Antibodies for Diagnostic or Therapeutic Use

Antibodies to the receptor proteins can also be generated which are useful in detection, characterization or isolation of receptor proteins, as well as for modifying receptor protein activity, in most cases, through inhibition of binding. Antibodies are generated by standard techniques, using human or animal receptor proteins. Since the proteins exhibit high evolutionary conservation, it may be advantageous to generate antibodies to a protein of a different species of origin than the species in which the antibodies are to be tested or utilized, looking for those antibodies which are immunoreactive with the most evolutionarily conserved regions. Antibodies are typically generated by immunization of an animal using an adjuvant such as Freund's adjuvant in combination with an immunogenic amount of the protein administered over a period of weeks in two to three week intervals, then isolated from the serum, or used to make hybridomas which express the antibodies in culture. Because the methods for immunizing animals yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarily-determining hypervariable regions (CDRs) are of non-human origin, whereas all framework regions (FR) of variable domains are products of human genes. These "humanized" antibodies present a lesser xenographic rejection stimulus when introduced to a human recipient.

To accomplish humanization of a selected mouse monoclonal antibody, the CDR grafting method described by Daugherty, et al., (1991) *Nucl. Acids Res.*, 19:2471–2476, incorporated herein by reference, may be used. Briefly, the variable region DNA of a selected animal recombinant anti-idiotypic ScFv is sequenced by the method of Clackson, T., et al., (1991) *Nature*, 352:624–688, incorporated herein by reference. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

The antibodies can be formulated in standard pharmaceutical carriers for administration to patients in need thereof. These include saline, phosphate buffered saline, and other aqueous carriers, and liposomes, polymeric microspheres and other controlled release delivery devices, as are well known in the art. The antibodies can also be administered with adjuvant, such as muramyl dipeptide or other materials approved for use in humans (Freund's adjuvant can be used for administration of antibody to animals).

Screening for drugs modifying or altering the extent of receptor function or expression The receptor proteins are useful as targets for compounds which turn on, or off, or otherwise regulate binding to these receptors. The assays described above clearly provide routine methodology by which a compound can be tested for an inhibitory effect on binding of PC or APC. The in vitro studies of compounds which appear to inhibit binding selectively to the receptors are then confirmed by animal testing. Since the molecules are so highly evolutionarily conserved, it is possible to conduct studies in laboratory animals such as mice to predict the effects in humans.

In cases where inflammatory mediators or vascular disease down regulate EPCR, it would be advantageous to increase its concentration in vivo on endothelium. The binding assays described here and the gene sequence allow assays for increased EPCR expression. Similar approaches have been taken with thrombomodulin and investigators have shown that cyclic AMP (Maruyama, I. et al. (1991) *Thrombosis Research* 61, 301–310) and interleukin 4 (Kapiotis,S. et al., (1991) *Blood* 78, 410–415) can elevate thrombomodulin expression. The ability to screen such drugs or drugs that block TNF down regulation of EPCR provide an approach to elevating EPCR expression in vivo and thus enhancing anticoagulant and anti-inflammatory activity.

Studies based on inhibition of binding are predictive for indirect effects of alteration of receptor binding. For example, inhibition of binding of APC or increased expression of TNF is predictive of inhibition of EPCR function.

Assays for testing compounds for useful activity can be based solely on interaction with the receptor protein, preferably expressed on the surface of transfected cells such as those described above. Proteins in solution or immobilized on inert substrates can also be utilized. These can be used to detect inhibition or enhancement in binding of PC or APC Alternatively, the assays can be based on interaction with the gene sequence encoding the receptor protein, preferably the regulatory sequences directing expression of the receptor protein. For example, antisense which binds to the regulatory sequences, and/or to the protein encoding sequences can be synthesized using standard oligonucleotide synthetic chemistry. The antisense can be stabilized for pharmaceutical use using standard methodology (encapsulation in a liposome or microsphere; introduction of modified nucleotides that are resistant to degradation or groups which increase resistance to endonucleases, such as phosphorothiodates and methylation), then screened initially for alteration of receptor activity in transfected or naturally occurring cells which express the receptor, then in vivo in laboratory animals. Typically, the antisense would inhibit expression. However, sequences which block those sequences which "turn off" synthesis can also be targeted.

The receptor protein for study can be isolated from either naturally occurring cells or cells which have been genetically engineered to express the receptor, as described in the examples above. In the preferred embodiment, the cells would have been engineered using the intact gene.

Random generation of receptor or receptor encoding sequence binding molecules.

Molecules with a given function, catalytic or ligand-binding, can be selected for from a complex mixture of random molecules in what has been referred to as "in vitro genetics" (Szostak, (1992) TIBS 19:89). One synthesizes a large pool of molecules bearing random and defined sequences and subjects that complex mixture, for example, approximately $10^{15}$ individual sequences in 100 μg of a 100 nucleotide RNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1992; Bock et al, 1992).

Computer assisted drug design

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., (1988) *Acta Pharmaceutica Fennica* 97, 159–166; Ripka, *New Scientist* 54–57 (Jun. 16, 1988); McKinaly and Rossmann, (1989) *Annu. Rev. Pharmacol. Toxiciol.* 29, 111–122; Perry and Davies, *QSAR: Quantitative Structure-Activity Relationships in Drug Design* pp. 189–193 (Alan R. Liss, Inc. 1989); Lewis and Dean, (1989) *Proc. R. Soc. Lond.* 236, 125–140 and 141–162; and, with respect to a model receptor for nucleic acid components, Askew, et al., (1989) *J. Am. Chem. Soc.* 111, 1082–1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Generation of nucleic acid regulators

Nucleic acid molecules containing the 5' regulatory sequences of the receptor genes can be used to regulate or inhibit gene expression in vivo. Vectors, including both plasmid and eukaryotic viral vectors, may be used to express a particular recombinant 5' flanking region-gene construct in cells depending on the preference and judgment of the skilled practitioner (see, e.g., Sambrook et al., Chapter 16). Furthermore, a number of viral and nonviral vectors are being developed that enable the introduction of nucleic acid sequences in vivo (see, e.g., Mulligan, (1993) *Science,* 260, 926–932; U.S. Pat. No. 4,980,286; U.S. Pat. No. 4,868,116; incorporated herein by reference). Recently, a delivery system was developed in which nucleic acid is encapsulated in cationic liposomes which can be injected intravenously into a mammal. This system has been used to introduce DNA into the cells of multiple tissues of adult mice, including endothelium and bone marrow (see, e.g., Zhu et al., (1993) *Science* 261, 209–211; incorporated herein by reference).

The 5' flanking sequences of the receptor gene can also be used to inhibit the expression of the receptor. For example, an antisense RNA of all or a portion of the 5' flanking region of the receptor gene can be used to inhibit expression of the receptor in vivo. Expression vectors (e.g., retroviral expression vectors) are already available in the art which can be used to generate an antisense RNA of a selected DNA sequence which is expressed in a cell (see, e.g., U.S. Pat. No. 4,868,116; U.S. Pat. No. 4,980,286). Accordingly, DNA containing all or a portion of the sequence of the 5' flanking region of the receptor gene can be inserted into an appropriate expression vector so that upon passage into the cell, the transcription of the inserted DNA yields an antisense RNA that is complementary to the mRNA transcript of the receptor protein gene normally found in the cell. This antisense RNA transcript of the inserted DNA can then base-pair with the normal mRNA transcript found in the cell and thereby prevent the mRNA from being translated. It is of course necessary to select sequences of the 5' flanking region that are downstream from the transcriptional start sites for the receptor protein gene to ensure that the antisense RNA contains complementary sequences present on the mRNA.

Antisense RNA can be generated in vitro also, and then inserted into cells. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication (see e.g., Zamecnik et al., (1978) *Proc. Natl. Acad. Sci. USA* 75, 280–284; Zamecnik et al., (1986) *Proc. Natl. Acad. Sci.,* 83, 4143–4146; Wickstrom et al., (1988) *Proc. Natl. Acad. Sci. USA* 85, 1028–1032; Crooke, (1993) *FASEB J.* 7, 533–539. Furthermore, recent work has shown that improved inhibition of expression of a gene by antisense oligonucleotides is possible if the antisense oligonucleotides contain modified nucleotides (see, e.g., Offensperger et. al., (1993) *EMBO J.* 12, 1257–1262 (in vivo inhibition of duck hepatitis B viral replication and gene expression by antisense phosphorothioate oligodeoxynucleotides); PCT WO 93/01286 Rosenberg et al., (synthesis of sulfurthioate oligonucleotides); Agrawal et al., (1988) *Proc. Natl. Acad. Sci. USA* 85, 7079–7083 (synthesis of antisense oligonucleoside phosphoramidates and phosphorothioates to inhibit replication of human immunodeficiency virus-1); Sarin et al., (1989) *Proc. Natl. Acad. Sci. USA* 85, 7448–7794 (synthesis of antisense methylphosphonate oligonucleotides); Shaw et al., (1991) *Nucleic Acids Res* 19, 747–750 (synthesis of 3' exonuclease-resistant oligonucleotides containing 3' terminal phosphoroamidate modifications); incorporated herein by reference).

The sequences of the 5' flanking region of receptor protein gene can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., Maher et al., (1989) *Science* 245, 725–730; Orson et al., (1991) *Nucl. Acids Res.* 19, 3435–3441; Postal et al., (1991) *Proc. Natl. Acad. Sci. USA* 88, 8227–8231; Cooney et al., (1988) *Science* 241, 456–459; Young et al., (1991) *Proc. Natl. Acad. Sci. USA* 88, 10023–10026; Duval-Valentin et al., (1992) *Proc. Natl. Acad. Sci. USA* 89, 504–508; Blume et al., (1992) *Nucl. Acids Res.* 20, 1777–1784; Grigoriev et al., (1992) *J. Biol. Chem.* 267, 3389–3395.

Recently, both theoretical calculations and empirical findings have been reported which provide guidance for the design of oligonucleotides for use in oligonucleotide-directed triple helix formation to inhibit gene expression. For example, oligonucleotides should generally be greater than 14 nucleotides in length to ensure target sequence specificity (see, e.g., Maher et al., (1989); Grigoriev et al., (1992)). Also, many cells avidly take up oligonucleotides that are less than 50 nucleotides in length (see e.g., Orson et al., (1991); Holt et al., (1988) *Mol. Cell. Biol.* 8, 963–973; Wickstrom et al., (1988) *Proc. Natl. Acad. Sci. USA* 85, 1028–1032). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., (1992).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., (1984) Ann. Rev. Biochem. 53, 323–356 (phosphotriester and phosphite-triester methods); Narang et al., (1980) Methods Enzymol., 65, 610–620 (phosphotriester method). Accordingly, DNA sequences of the 5' flanking region of the receptor protein gene described herein can be used to design and construct oligonucleotides including a DNA sequence consisting essentially of at least 15 consecutive nucleotides, with or without base modifications or intercalating agent derivatives, for use in forming triple helices specifically within the 5' flanking region of a receptor protein gene in order to inhibit expression of the gene.

In some cases it may be advantageous to insert enhancers or multiple copies of the regulatory sequences into an expression system to facilitate screening of methods and reagents for manipulation of expression.

Preparation of Receptor Protein Fragments

Compounds which are effective for blocking binding of the receptor can also consist of fragments of the receptor proteins, expressed recombinantly and cleaved by enzymatic digest or expressed from a sequence encoding a peptide of less than the full length receptor protein. These will typically be soluble proteins, i.e., not including the transmembrane and cytoplasmic regions, although smaller portions determined in the assays described above to inhibit or compete for binding to the receptor proteins can also be utilized. It is a routine matter to make appropriate receptor protein fragments, test for binding, and then utilize. The preferred fragments are of human origin, in order to minimize potential immunological response. The peptides can be as short as five to eight amino acids in length and are easily prepared by standard techniques. They can also be modified to increase in vivo half-life, by chemical modification of the amino acids or by attachment to a carrier molecule or inert substrate. Based on studies with other peptide fragments blocking receptor binding, the $IC_{50}$, the dose of peptide required to inhibit binding by 50%, ranges from about 1 μM to greater than 10 mM, depending on the peptide size and folding. These ranges are well within the effective concentrations for the in vivo administration of peptides, based on comparison with the RGD-containing peptides, described, for example, in U.S. Pat. No. 4,792,525 to Ruoslaghti, et al., used in vivo to alter cell attachment and phagocytosis. The peptides can also be conjugated to a carrier protein such as keyhole limpet hemocyanin by its N-terminal cysteine by standard procedures such as the commercial Imject kit from Pierce Chemicals or expressed as a fusion protein, which may have increased efficacy.

As noted above, the peptides can be prepared by proteolytic cleavage of the receptor proteins, or, preferably, by synthetic means. These methods are known to those skilled in the art. An example is the solid phase synthesis described by J. Merrifield, (1964) J. Am. Chem. Soc. 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891. These methods can be used to synthesize peptides having identical sequence to the receptor proteins described herein, or substitutions or additions of amino acids, which can be screened for activity as described above.

The peptide can also be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

The peptides are generally active when administered parenterally in amounts above about 1 μg/kg of body weight. Based on extrapolation from other proteins, for treatment of most inflammatory disorders, the dosage range will be between 0.1 to 70 mg/kg of body weight. This dosage will be dependent, in part, on whether one or more peptides are administered.

Pharmaceutical Compositions

Compounds which alter receptor protein binding are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", Drug Carriers in Biology and Medicine pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

Disorders to be treated

As described herein, a variety of compounds can be used to inhibit or enhance expression of the EPCR. The nature of the disorder will determine if the expression should be enhanced or inhibited. For example, based on the studies involving the use of an anti-protein C antibody in combination with cytokine, it should be possible to treat solid tumors by enhancing an inflammatory response involving blocking of protein C or activated protein C binding to an endothelial cell protein C/activated protein C receptor by administering to a patient in need of treatment thereof an amount of a compound blocking binding of protein C or activated protein C to the receptor. Similarly, it should be possible to treat disorders such as gram negative sepsis, stroke, thrombosis, septic shock, adult respiratory distress syndrome, and pulmonary emboli using a method for inhibiting an inflammatory response involving administration of EPCR or EPCR fragments or substances that upregulate EPCR expression to a patient in need of treatment therof.

Modifications and variations of the methods and materials described herein will be obvious to those skilled in the art and are intended to be encompassed by the following claims. The teachings of the references cited herein are specifically incorporated herein.

We claim:

1. An isolated nucleic acid molecule encoding the amino acid sequence set forth in SEQ ID No. 2.

2. The nucleic acid molecule of claim 1 further comprising an expression vector.

3. An expression host comprising the nucleic acid molecule of claim 2.

4. The expression host of claim 3 wherein the expression host is a non-human cell or a non-endothelial cell.

5. The nucleic acid molecule of claim 1 labelled with a detectable label.

6. An isolated nucleic acid molecule as set forth in SEQ ID No. 1 encoding an endothelial cell protein C/activated protein C receptor protein.

7. An isolated nucleic acid molecule encoding the amino acid sequence of SEQ ID No. 2 amino sequence having conservative substitutions, additions or from amino acid residues 1 to 210 of SEQ ID NO: 2.

8. The nucleic acid molecule of claim 7 further comprising an expression vector.

9. An expression host comprising the nucleic acid molecule of claim 8.

10. The expression host of claim 9 wherein the expression host is a non-human cell or a non-endothelial cell.

11. The nucleic acid molecule of claim 7 labelled with a detectable label.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 1302 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: misc_feature
( B ) LOCATION: 1..1302
( D ) OTHER INFORMATION: /note="Nucleotides 25 through 738 encode the Endothelial Cell Protein Receptor of Sequence ID No. 2."

( x i ) SEQUENCE DESCRIPTION: SEQ ID NO:1:

```
CAGGTCCGGA GCCTCAACTT CAGGATGTTG ACAACATTGC TGCCGATACT GCTGCTGTCT    60
GGCTGGGCCT TTTGTAGCCA AGACGCCTCA GATGGCCTCC AAAGACTTCA TATGCTCCAG   120
ATCTCCTACT TCCGCGACCC CTATCACGTG TGGTACCAGG GCAACGCGTC GCTGGGGGGA   180
CACCTAACGC ACGTGCTGGA AGGCCCAGAC ACCAACACCA CGATCATTCA GCTGCAGCCC   240
TTGCAGGAGC CCGAGAGCTG GGCGCGCACG CAGAGTGGCC TGCAGTCCTA CCTGCTCCAG   300
TTCCACGGCC TCGTGCGCCT GGTGCACCAG GAGCGGACCT TGGCCTTTCC TCTGACCATC   360
CGCTGCTTCC TGGGCTGTGA GCTGCCTCCC GAGGGCTCTA GAGCCCATGT CTTCTTCGAA   420
GTGGCTGTGA ATGGGAGCTC CTTTGTGAGT TTCCGGCCGG AGAGAGCCTT GTGGCAGGCA   480
GACACCCAGG TCACCTCCGG AGTGGTCACC TTCACCCTGC AGCAGCTCAA TGCCTACAAC   540
CGCACTCGGT ATGAACTGCG GGAATTCCTG GAGGACACCT GTGTGCAGTA TGTGCAGAAA   600
CATATTTCCG CGGAAAACAC GAAAGGGAGC CAAACAAGCC GCTCCTACAC TTCGCTGGTC   660
CTGGGCGTCC TGGTGGGCGG TTTCATCATT GCTGGTGTGG CTGTAGGCAT CTTCCTGTGC   720
ACAGGTGGAC GGCGATGTTA ATTACTCTCC AGCCCCGTCA GAAGGGGCTG GATTGATGGA   780
GGCTGGCAAG GGAAAGTTTC AGCTCACTGT GAAGCCAGAC TCCCCAACTG AAACACCAGA   840
```

```
AGGTTTGGAG TGACAGCTCC TTTCTTCTCC CACATCTGCC CACTGAAGAT TTGAGGGAGG      900

GGAGATGGAG AGGAGAGGTG GACAAAGTAC TTGGTTTGCT AAGAACCTAA GAACGTGTAT      960

GCTTTGCTGA ATTAGTCTGA TAAGTGAATG TTTATCTATC TTTGTGGAAA ACAGATAATG     1020

GAGTTGGGGC AGGAAGCCTA TGCGCCATCC TCCAAAGACA GACAGAATCA CCTGAGGCGT     1080

TCAAAAGATA TAACCAAATA AACAAGTCAT CCACAATCAA AATACAACAT TCAATACTTC     1140

CAGGTGTGTC AGACTTGGGA TGGGACGCTG ATATAATAGG GTAGAAAGAA GTAACACGAA     1200

GAAGTGGTGG AAATGTAAAA TCCAAGTCAT ATGGCAGTGA TCAATTATTA ATCAATTAAT     1260

AATATTAATA AATTTCTTAT ATTTAAAAAA AAAAAAAAA AA                        1302
```

(2) INFORMATION FOR SEQ ID NO:2:

(i) SEQUENCE CHARACTERISTICS:
        (A) LENGTH: 238 amino acids
        (B) TYPE: amino acid
        (D) TOPOLOGY: linear (ii) MOLECULE TYPE: protein (iii) HYPOTHETICAL: NO (ix) FEATURE:
        (A) NAME/KEY: misc_feature
        (B) LOCATION: 1..365
        (D) OTHER INFORMATION: /note="Endothelial Cell Protein
        Receptor encoded by nucleotides 1 through 1302 of
        Sequence ID No. 1."

(ix) FEATURE:
        (A) NAME/KEY: Modified-site
        (B) LOCATION: 1..15
        (D) OTHER INFORMATION: /note="Amino acids 1-15 represent
        a putative signal sequence."

(ix) FEATURE:
        (A) NAME/KEY: Domain
        (B) LOCATION: 211..236
        (D) OTHER INFORMATION: /note="Amino acids 211-236
        represent a putative transmembrane domain."

(ix) FEATURE:
        (A) NAME/KEY: Active-site
        (B) LOCATION: 47..174
        (D) OTHER INFORMATION: /note="Amino acids 47-49, 64-66,
        136-138 and 172-174 represent potential
        N- glycosylation sites."

(ix) FEATURE:
        (A) NAME/KEY: Modified-site
        (B) LOCATION: 17..186
        (D) OTHER INFORMATION: /note="Amino acids 17, 114, 118
        and 186 represent extracellular cysteine
        residues."

(xi) SEQUENCE DESCRIPTION: SEQ ID NO:2:

```
Met Leu Thr Thr Leu Leu Pro Ile Leu Leu Leu Ser Gly Trp Ala Phe
 1               5                  10                  15

Cys Ser Gln Asp Ala Ser Asp Gly Leu Gln Arg Leu His Met Leu Gln
             20                  25                  30

Ile Ser Tyr Phe Arg Asp Pro Tyr His Val Trp Tyr Gln Gly Asn Ala
         35                  40                  45

Ser Leu Gly Gly His Leu Thr His Val Leu Glu Gly Pro Asp Thr Asn
     50                  55                  60

Thr Thr Ile Ile Gln Leu Gln Pro Leu Gln Glu Pro Glu Ser Trp Ala
65                   70                  75                  80

Arg Thr Gln Ser Gly Leu Gln Ser Tyr Leu Leu Gln Phe His Gly Leu
```

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |
| Val | Arg | Leu | Val | His | Gln | Glu | Arg | Thr | Leu | Ala | Phe | Pro | Leu | Thr | Ile |
|     |     |     | 100 |     |     |     |     | 105 |     |     |     |     | 110 |     |     |
| Arg | Cys | Phe | Leu | Gly | Cys | Glu | Leu | Pro | Pro | Glu | Gly | Ser | Arg | Ala | His |
|     |     |     | 115 |     |     |     |     | 120 |     |     |     |     | 125 |     |     |
| Val | Phe | Phe | Glu | Val | Ala | Val | Asn | Gly | Ser | Ser | Phe | Val | Ser | Phe | Arg |
|     |     |     | 130 |     |     |     | 135 |     |     |     |     | 140 |     |     |     |
| Pro | Glu | Arg | Ala | Leu | Trp | Gln | Ala | Asp | Thr | Gln | Val | Thr | Ser | Gly | Val |
| 145 |     |     |     |     | 150 |     |     |     |     | 155 |     |     |     |     | 160 |
| Val | Thr | Phe | Thr | Leu | Gln | Gln | Leu | Asn | Ala | Tyr | Asn | Arg | Thr | Arg | Tyr |
|     |     |     |     | 165 |     |     |     |     | 170 |     |     |     |     | 175 |     |
| Glu | Leu | Arg | Glu | Phe | Leu | Glu | Asp | Thr | Cys | Val | Gln | Tyr | Val | Gln | Lys |
|     |     |     | 180 |     |     |     |     | 185 |     |     |     |     | 190 |     |     |
| His | Ile | Ser | Ala | Glu | Asn | Thr | Lys | Gly | Ser | Gln | Thr | Ser | Arg | Ser | Tyr |
|     |     |     | 195 |     |     |     | 200 |     |     |     |     | 205 |     |     |     |
| Thr | Ser | Leu | Val | Leu | Gly | Val | Leu | Val | Gly | Gly | Phe | Ile | Ile | Ala | Gly |
|     |     |     | 210 |     |     |     | 215 |     |     |     |     | 220 |     |     |     |
| Val | Ala | Val | Gly | Ile | Phe | Leu | Cys | Thr | Gly | Gly | Arg | Arg | Cys |     |     |
| 225 |     |     |     |     | 230 |     |     |     |     | 235 |     |     |     |     |     |

( 2 ) INFORMATION FOR SEQ ID NO:3:

( i ) SEQUENCE CHARACTERISTICS:
( A ) LENGTH: 244 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

| Met | Leu | Thr | Lys | Phe | Leu | Leu | Leu | Leu | Leu | Leu | Leu | Leu | Pro | Gly | Cys |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ala | Phe | Val | Thr | Pro | Met | Ala | Pro | Lys | Ala | Ala | Tyr | Ala | Pro | Asp | Leu |
|     |     |     | 20  |     |     |     |     | 25  |     |     |     |     | 30  |     |     |
| Leu | Phe | Pro | Arg | Pro | Pro | Ser | Cys | Glu | Ala | Ser | Gly | Gln | Arg | Ser | Leu |
|     |     |     | 35  |     |     |     |     | 40  |     |     |     |     | 45  |     |     |
| Gly | Lys | Leu | Leu | Thr | His | Thr | Leu | Glu | Gly | Pro | Ser | Gln | Asn | Val | Thr |
|     | 50  |     |     |     |     | 55  |     |     |     |     | 60  |     |     |     |     |
| Ile | Leu | Gln | Leu | Gln | Pro | Trp | Gln | Asp | Pro | Glu | Ser | Trp | Glu | Arg | Thr |
| 65  |     |     |     |     | 70  |     |     |     |     | 75  |     |     |     |     | 80  |
| Glu | Ser | Gly | Leu | Gln | Ile | Tyr | Leu | Thr | Gln | Phe | Glu | Ser | Leu | Val | Lys |
|     |     |     |     | 85  |     |     |     |     | 90  |     |     |     |     | 95  |     |
| Leu | Val | Tyr | Arg | Glu | Arg | Lys | Glu | Asn | Val | Phe | Phe | Pro | Leu | Thr | Val |
|     |     |     | 100 |     |     |     |     | 105 |     |     |     |     | 110 |     |     |
| Ser | Cys | Ser | Leu | Gly | Cys | Glu | Leu | Pro | Glu | Glu | Glu | Glu | Glu | Gly | Ser |
|     |     |     | 115 |     |     |     |     | 120 |     |     |     |     | 125 |     |     |
| Glu | Pro | His | Val | Phe | Phe | Asp | Val | Ala | Val | Asn | Gly | Ser | Ala | Phe | Val |
|     |     |     | 130 |     |     |     | 135 |     |     |     |     | 140 |     |     |     |
| Ser | Phe | Arg | Pro | Lys | Thr | Ala | Val | Trp | Val | Ser | Gly | Ser | Gln | Glu | Pro |
| 145 |     |     |     |     | 150 |     |     |     |     | 155 |     |     |     |     | 160 |
| Ser | Lys | Ala | Ala | Asn | Phe | Thr | Leu | Lys | Gln | Leu | Asn | Ala | Tyr | Asn | Arg |
|     |     |     |     | 165 |     |     |     |     | 170 |     |     |     |     | 175 |     |
| Thr | Arg | Tyr | Glu | Leu | Gln | Glu | Phe | Leu | Gln | Asp | Thr | Cys | Val | Glu | Phe |
|     |     |     | 180 |     |     |     |     | 185 |     |     |     |     | 190 |     |     |
| Leu | Glu | Asn | His | Ile | Thr | Thr | Gln | Asn | Met | Lys | Gly | Ser | Gln | Thr | Gly |
|     |     |     | 195 |     |     |     | 200 |     |     |     |     | 205 |     |     |     |

```
Arg  Ser  Tyr  Thr  Ser  Leu  Val  Leu  Gly  Ile  Leu  Met  Gly  Cys  Phe  Ile
     210                      215                      220

Ile  Ala  Gly  Val  Ala  Val  Gly  Ile  Phe  Met  Cys  Thr  Ser  Gly  Arg  Gly
225                      230                      235                      240

Leu  Leu  Ile  Ile
```

( 2 ) INFORMATION FOR SEQ ID NO:4:-

( i ) SEQUENCE CHARACTERISTICS:
      ( A ) LENGTH: 335 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:4:

```
Met  Gly  Cys  Leu  Leu  Phe  Leu  Leu  Leu  Trp  Ala  Leu  Leu  Gln  Ala  Trp
1                   5                        10                       15

Gly  Ser  Ala  Glu  Val  Pro  Gln  Arg  Leu  Phe  Pro  Leu  Arg  Cys  Leu  Gln
               20                       25                       30

Ile  Ser  Ser  Phe  Ala  Asn  Ser  Ser  Trp  Thr  Arg  Thr  Asp  Gly  Leu  Ala
          35                        40                       45

Trp  Leu  Gly  Glu  Leu  Gln  Thr  His  Ser  Trp  Ser  Asn  Asp  Ser  Asp  Thr
     50                        55                       60

Val  Arg  Ser  Leu  Lys  Pro  Trp  Ser  Gln  Gly  Thr  Phe  Ser  Asp  Gln  Gln
65                       70                       75                       80

Trp  Glu  Thr  Leu  Gln  His  Ile  Phe  Arg  Val  Tyr  Arg  Ser  Ser  Phe  Thr
                    85                       90                       95

Arg  Asp  Val  Lys  Glu  Phe  Ala  Lys  Met  Leu  Arg  Leu  Ser  Tyr  Pro  Leu
               100                      105                      110

Glu  Leu  Gln  Val  Ser  Ala  Gly  Cys  Glu  Val  His  Pro  Gly  Asn  Ala  Ser
          115                      120                      125

Asn  Asn  Phe  Phe  His  Val  Ala  Phe  Gln  Gly  Lys  Asp  Ile  Leu  Ser  Phe
     130                      135                      140

Gln  Gly  Thr  Ser  Trp  Glu  Pro  Thr  Gln  Glu  Ala  Pro  Leu  Trp  Val  Asn
145                      150                      155                      160

Leu  Ala  Ile  Gln  Val  Leu  Asn  Gln  Asp  Lys  Trp  Thr  Arg  Glu  Thr  Val
               165                      170                      175

Gln  Trp  Leu  Leu  Asn  Gly  Thr  Cys  Pro  Gln  Phe  Val  Ser  Gly  Leu  Leu
          180                      185                      190

Glu  Ser  Gly  Lys  Ser  Glu  Leu  Lys  Lys  Gln  Val  Lys  Pro  Lys  Ala  Trp
     195                      200                      205

Leu  Ser  Arg  Gly  Pro  Ser  Pro  Gly  Pro  Gly  Arg  Leu  Leu  Leu  Val  Cys
     210                      215                      220

His  Val  Ser  Gly  Phe  Tyr  Pro  Lys  Pro  Val  Trp  Val  Lys  Trp  Met  Arg
225                      230                      235                      240

Gly  Glu  Gln  Glu  Gln  Gln  Gly  Thr  Gln  Pro  Gly  Asp  Ile  Leu  Pro  Asn
                    245                      250                      255

Ala  Asp  Glu  Thr  Trp  Tyr  Leu  Arg  Ala  Thr  Leu  Asp  Val  Val  Ala  Gly
               260                      265                      270

Glu  Ala  Ala  Gly  Leu  Ser  Cys  Arg  Val  Lys  His  Ser  Ser  Leu  Glu  Gly
          275                      280                      285

Gln  Asp  Ile  Val  Leu  Tyr  Trp  Gly  Gly  Ser  Tyr  Thr  Ser  Met  Gly  Leu
     290                      295                      300

Ile  Ala  Leu  Ala  Val  Leu  Ala  Cys  Leu  Leu  Phe  Leu  Leu  Ile  Val  Gly
```

```
                    305                         310                     315                         320
             Phe  Thr  Ser  Arg  Phe  Lys  Arg  Gln  Thr  Ser  Tyr  Gln  Gly  Val  Leu
                                325                      330                      335
```

( 2 ) INFORMATION FOR SEQ ID NO:5:

( i ) SEQUENCE CHARACTERISTICS:
        ( A ) LENGTH: 336 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met  Arg  Tyr  Leu  Pro  Cys  Leu  Leu  Leu  Trp  Ala  Phe  Leu  Gln  Val  Trp
 1                    5                        10                       15

Gly  Gln  Ser  Glu  Val  Gln  Gln  Lys  Asn  Tyr  Thr  Phe  Arg  Cys  Leu  Gln
               20                       25                       30

Thr  Ser  Ser  Phe  Ala  Asn  Ile  Ser  Trp  Ser  Arg  Thr  Asp  Ser  Leu  Ile
          35                       40                       45

Leu  Leu  Gly  Asp  Leu  Gln  Thr  His  Arg  Trp  Ser  Asn  Asp  Ser  Ala  Thr
     50                       55                       60

Ile  Ser  Phe  Thr  Lys  Pro  Trp  Ser  Gln  Gly  Lys  Leu  Ser  Asn  Gln  Gln
 65                       70                       75                       80

Trp  Glu  Lys  Leu  Gln  His  Met  Phe  Gln  Val  Tyr  Arg  Val  Ser  Phe  Thr
                    85                       90                       95

Arg  Asp  Ile  Gln  Glu  Leu  Val  Lys  Met  Met  Ser  Pro  Lys  Glu  Asp  Tyr
               100                      105                      110

Pro  Ile  Glu  Ile  Gln  Leu  Ser  Thr  Gly  Cys  Glu  Met  Tyr  Pro  Gly  Asn
          115                      120                      125

Ala  Ser  Glu  Ser  Phe  Phe  His  Val  Ala  Phe  Gln  Gly  Lys  Tyr  Ala  Val
     130                      135                      140

Arg  Phe  Arg  Gly  Thr  Ser  Trp  Gln  Arg  Val  Leu  Gly  Ala  Pro  Ser  Trp
145                       150                      155                      160

Leu  Asp  Leu  Pro  Ile  Lys  Val  Leu  Asn  Ala  Asp  Gln  Gly  Thr  Ser  Ala
                    165                      170                      175

Thr  Val  Gln  Thr  Leu  Leu  Asn  Asp  Thr  Trp  Pro  Gln  Phe  Ala  Arg  Gly
               180                      185                      190

Leu  Leu  Glu  Ala  Gly  Lys  Ser  Asp  Leu  Glu  Lys  Gln  Glu  Lys  Pro  Val
          195                      200                      205

Ala  Trp  Leu  Ser  Ser  Val  Pro  Ser  Ser  Ala  His  Gly  His  Leu  Gln  Leu
     210                      215                      220

Val  Cys  His  Val  Ser  Gly  Phe  Tyr  Pro  Lys  Pro  Val  Trp  Val  Met  Trp
225                       230                      235                      240

Met  Arg  Gly  Asp  Gln  Glu  Gln  Gln  Gly  Thr  His  Arg  Gly  Asp  Phe  Leu
                    245                      250                      255

Pro  Asn  Ala  Asp  Glu  Thr  Trp  Tyr  Leu  Gln  Ala  Thr  Leu  Asp  Val  Glu
               260                      265                      270

Ala  Gly  Glu  Glu  Ala  Gly  Leu  Ala  Cys  Arg  Val  Lys  His  Ser  Ser  Leu
          275                      280                      285

Gly  Gly  Gln  Asp  Ile  Ile  Leu  Tyr  Trp  Asp  Ala  Arg  Gln  Ala  Pro  Val
     290                      295                      300

Gly  Leu  Ile  Val  Phe  Ile  Val  Leu  Ile  Met  Leu  Val  Val  Val  Gly  Ala
305                       310                      315                      320

Val  Val  Tyr  Tyr  Ile  Trp  Arg  Arg  Arg  Ser  Ala  Tyr  Gln  Asp  Ile  Arg
                    325                      330                      335
```

( 2 ) INFORMATION FOR SEQ ID NO:6:

( i ) SEQUENCE CHARACTERISTICS:
    ( A ) LENGTH: 242 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

```
Met Leu Thr Lys Phe Leu Pro Leu Leu Leu Leu Leu Pro Gly Cys
 1           5                   10                  15

Ala Leu Cys Asn Ser Asp Gly Ser Gln Ser Leu His Met Leu Gln Ile
            20                  25                  30

Ser Tyr Phe Gln Asp His His His Val Arg His Gln Gly Asn Ala Ser
        35                  40                      45

Leu Gly Lys Leu Leu Thr His Thr Leu Glu Gly Pro Ser Gln Asn Val
    50                  55                  60

Thr Ile Leu Gln Leu Gln Pro Trp Gln Asp Pro Glu Ser Trp Glu Arg
65                  70              75                      80

Thr Glu Ser Gly Leu Gln Ile Tyr Leu Thr Gln Phe Glu Ser Leu Val
                85                  90                  95

Lys Leu Val Tyr Arg Glu Arg Lys Glu Asn Val Phe Phe Pro Leu Thr
            100             105                     110

Val Ser Cys Ser Leu Gly Cys Glu Leu Pro Glu Glu Glu Glu Glu Gly
        115             120                 125

Ser Glu Pro His Val Phe Phe Asp Val Ala Val Asn Gly Ser Ala Phe
    130                 135             140

Val Ser Phe Arg Pro Lys Thr Ala Val Trp Val Ser Gly Ser Gln Glu
145             150                 155                     160

Pro Ser Lys Ala Ala Asn Phe Thr Leu Lys Gln Leu Asn Ala Tyr Asn
            165                 170                     175

Arg Thr Arg Tyr Glu Leu Gln Glu Phe Leu Gln Asp Thr Cys Val Glu
            180                 185                 190

Phe Leu Glu Asn His Ile Thr Thr Gln Asn Met Lys Gly Ser Gln Thr
            195                 200             205

Gly Arg Ser Tyr Thr Ser Leu Val Leu Gly Ile Leu Met Gly Cys Phe
    210                 215                 220

Ile Ile Ala Gly Val Ala Val Gly Ile Phe Met Cys Thr Ser Gly Arg
225                 230             235                     240

Arg Cys
```